(12) United States Patent
Bolle et al.

(10) Patent No.: US 7,214,742 B2
(45) Date of Patent: May 8, 2007

(54) 2-HYDROXYPHENYL-S-TRIAZINE CROSSLINKERS FOR POLYMER NETWORKS

(75) Inventors: Thomas Bolle, Efringen-Kirchen (DE); Andreas Valet, Binzen (DE); David George Leppard, Marly (CH); Stephen Mark Andrews, New Fairfield, CT (US); Ramanathan Ravichandran, Suffern, NY (US); Markus Grob, Riehen (CH); Dirk Simon, Mutterstadt (DE)

(73) Assignee: Ciba Specialty Chemicals Corp., Tarrytown, NY (US)

( * ) Notice: Subject to any disclaimer, the term of this patent is extended or adjusted under 35 U.S.C. 154(b) by 334 days.

(21) Appl. No.: 10/497,297

(22) PCT Filed: Nov. 21, 2002

(86) PCT No.: PCT/EP02/13063

§ 371 (c)(1),
(2), (4) Date: May 26, 2004

(87) PCT Pub. No.: WO03/046068

PCT Pub. Date: Jun. 5, 2003

(65) Prior Publication Data

US 2005/0075465 A1 Apr. 7, 2005

(30) Foreign Application Priority Data

Nov. 30, 2001 (EP) .................................. 01811163

(51) Int. Cl.
C08K 5/3492 (2006.01)
C07D 251/24 (2006.01)

(52) U.S. Cl. ...................... 525/437; 544/215; 525/340; 525/360; 524/100; 524/89; 524/91; 524/95; 524/102; 524/103; 524/115

(58) Field of Classification Search ................ 525/437, 525/340, 360; 544/216, 215; 524/100, 89, 524/91, 95, 102, 103, 115
See application file for complete search history.

(56) References Cited

U.S. PATENT DOCUMENTS

| | | | |
|---|---|---|---|
| 3,244,708 A * | 4/1966 | Duennenberger et al. ... | 544/216 |
| 3,268,474 A | 8/1966 | Hardy et al. ................ | 260/45.8 |
| 4,826,978 A | 5/1989 | Migdal et al. ............... | 544/216 |
| 4,962,142 A | 10/1990 | Migdal et al. ............... | 524/100 |
| 5,189,084 A | 2/1993 | Birbaum et al. ............ | 524/100 |
| 5,322,868 A * | 6/1994 | Valet et al. .................. | 524/89 |
| 5,538,840 A | 7/1996 | Van Toan et al. ............ | 430/5.2 |
| 5,621,052 A | 4/1997 | Szita et al. .................. | 525/509 |
| 5,637,706 A * | 6/1997 | Stevenson et al. .......... | 544/216 |
| 5,672,704 A | 9/1997 | Toan et al. .................. | 544/215 |
| 5,859,073 A | 1/1999 | Pfaendner et al. ........... | 521/48 |

(Continued)

FOREIGN PATENT DOCUMENTS

EP 0434608 6/1991

(Continued)

Primary Examiner—Randy Gulakowski
Assistant Examiner—A. Toscano
(74) Attorney, Agent, or Firm—Tyler A. Stevenson

(57) ABSTRACT

Compounds of the general formula I'

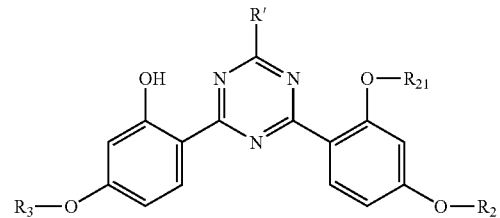

(I)

in which
$R^1$ is H, $C_1$–$C_{12}$alkyl; $C_5$–$C_{12}$cycloalkyl; $C_2$–$C_{18}$alkyl which is interrupted by one or more O; $SR_4$; $OR_5$; or is a group of formula II or III

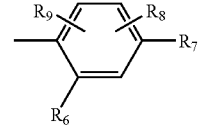

(II)

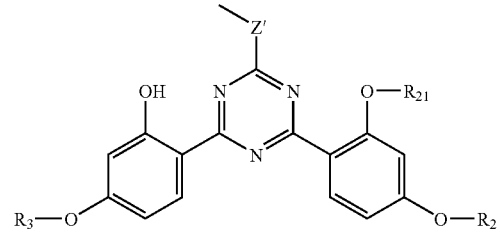

(III)

$R_2$, $R_{21}$ and $R_3$ independently of one another, are H or —Y—T as defined in claim 1, where T is a reactive group selected from OH, acryl- and methacryloxy and arylcarbonate groups, and further symbols are as defined in claim 1, are effective as crosslinking agents for polymeric networks, especially as in flexographic printing plates, coatings, and plastic containers or films.

Further provided is a method of protecting the content of a clear or lightly colored plastic container or film against the deleterious effects of ultraviolet radiation, which method comprises permanently and covalently bonding one or more UV absorbing moieties of a durable s-triazine UV absorber via condensation to a suitable polymer component.

14 Claims, No Drawings

U.S. PATENT DOCUMENTS

| | | | |
|---|---|---|---|
| 6,166,148 A * | 12/2000 | Ohrbom et al. | 525/326.7 |
| 6,242,597 B1 * | 6/2001 | Gupta et al. | 544/216 |
| 6,265,533 B1 | 7/2001 | Regel et al. | 528/487 |
| 6,284,821 B1 * | 9/2001 | Huglin et al. | 524/100 |
| 6,469,078 B1 | 10/2002 | Simon et al. | 524/139 |
| 6,602,447 B2 * | 8/2003 | Danielson et al. | 252/589 |
| 6,653,484 B2 * | 11/2003 | Toan et al. | 548/259 |
| 2001/0031866 A1 * | 10/2001 | Gupta et al. | 544/215 |
| 2001/0037022 A1 * | 11/2001 | Gupta et al. | 544/215 |

FOREIGN PATENT DOCUMENTS

| | | | |
|---|---|---|---|
| EP | 434608 A | * | 6/1991 |
| WO | 99/67246 | | 12/1999 |

\* cited by examiner

2-HYDROXYPHENYL-S-TRIAZINE CROSSLINKERS FOR POLYMER NETWORKS

The invention relates to a novel process for crosslinking organic polymers, the corresponding compositions, and to the use of specific multifunctional stabilizers of the 2-hydroxyphenyl-s-triazine class.

When it is desired to increase the stability of an organic polymer to light, oxygen and/or heat, it is common to add a stabilizer. One important group of light stabilizers are UV absorbers of the triphenyl-s-triazines, some of which have already been grafted onto polymeric substrates as described in the publications U.S. Pat. No. 5,189,084; U.S. Pat. No. 5,621,052; WO 99/67246; U.S. Pat. No. 5,538,840; U.S. Pat. No. 5,672,704; U.S. Pat. No. 6,166,148.

There is still need to obtain a system wherein better fixation of the light stabilizer, especially the UV absorber, in the polymer matrix is achieved.

Specific compounds from the class of the trisaryl-s-triazines have now been found which, surprisingly, possess particularly good crosslinking properties besides retaining their activity as light stabilizers.

The invention therefore provides a process for crosslinking an organic polymer by reacting a monomer, oligomer and/or polymer with a crosslinking agent, characterized in that the crosslinking agent is of the formula I' or I"

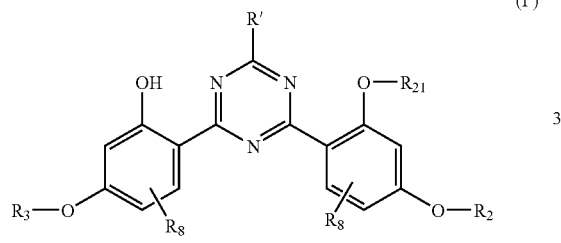

(I')

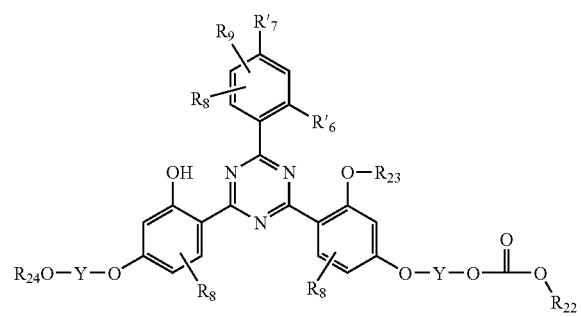

(I")

in which
R' is H, $C_1$–$C_{12}$alkyl; $C_5$–$C_{12}$cycloalkyl; $C_2$–$C_{18}$alkyl which is interrupted by one or more O; $SR_4$; $OR_5$; or is a group of formula II or III

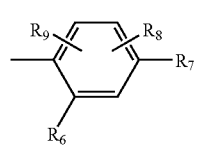

(II)

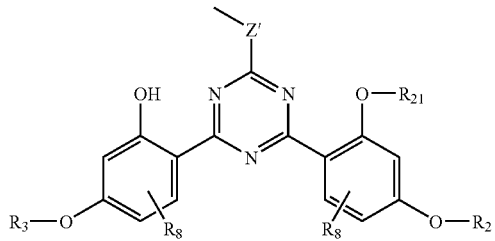

(III)

$R_2$ and $R_3$ each are —Y—T;
or where $R_{10}$ is a group of formula V, $R_{21}$ is H or —Y—T;
$R_4$ is $C_1$–$C_8$alkyl; or phenyl;
$R_5$ is $C_1$–$C_{12}$alkyl; $C_5$–$C_{12}$cycloalkyl; or $C_2$–$C_{18}$alkyl which is interrupted by one or more —O—;
$R_6$ is H; OH; $C_1$–$C_{12}$alkyl; $C_5$–$C_{12}$cycloalkyl; O—Y—T;
$R'_6$ is H; OH; $C_1$–$C_{12}$alkyl; $C_5$–$C_{12}$cycloalkyl; —O—Y—O—CO—O—$R_{22}$;
$R_7$ is H; OH; $C_1$–$C_{12}$alkyl; $C_5$–$C_{12}$cycloalkyl; phenyl; $OR_{10}$; $OCO$—$R_{11}$; $NR_{12}$—CO—$R_{11}$; $SR_4$;
$R'_7$ is H; OH; $C_1$–$C_{12}$alkyl; $C_5$–$C_{12}$cycloalkyl; phenyl; $OR'_{10}$; $R_8$ and $R_9$ independently are H or $C_1$–$C_{12}$alkyl or $C_7$–$C_{12}$aralkyl;
$R_{10}$ is $C_1$–$C_{12}$alkyl; $C_2$–$C_{10}$alkenyl; $C_5$–$C_{12}$cycloalkyl; Y—T; or a group of the formula V

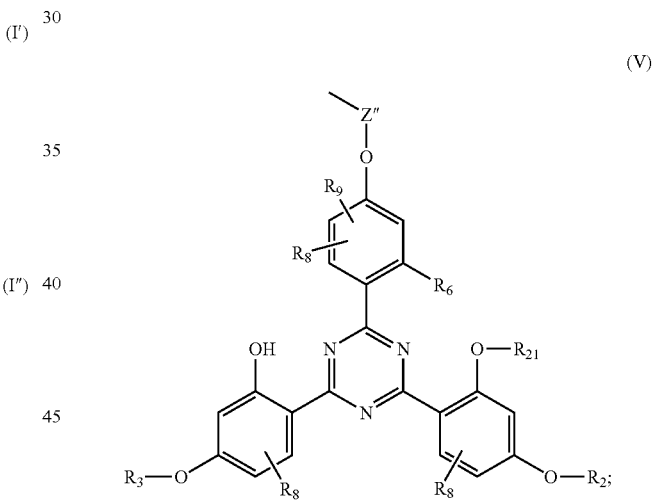

(V)

$R'_{10}$ is $C_1$–$C_{12}$alkyl; $C_2$–$C_{10}$alkenyl; $C_5$–$C_{12}$cycloalkyl; —Y—O—CO—O—$R_{22}$;
$R_{11}$ is $C_1$–$C_{12}$alkyl; $C_5$–$C_{12}$cycloalkyl; $C_2$–$C_6$alkenyl; $C_1$–$C_{12}$alkoxy;
$R_{12}$ is H; $C_1$–$C_{12}$alkyl; $C_5$–$C_{12}$cycloalkyl;
$R_{13}$ is $C_1$–$C_{18}$alkyl; phenyl; $C_7$–$C_{12}$alkylphenyl; benzyl;
$R_{17}$ is H, $C_1$–$C_8$alkyl; $C_2$–$C_8$alkyl substituted by OH; $C_5$–$C_{12}$cycloalkyl; or is $(CH_2CH_2O)_m$—H, wherein m ranges from 2 to 9;
$R_{21}$ is —Y—T; and when R' is the group

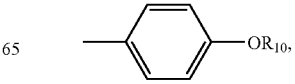

$R_{21}$ is H or —Y—T;

$R_{22}$ is phenyl or naphthyl, or phenyl or naphthyl each of which is substituted by $C_1$–$C_{18}$alkyl, $C_5$–$C_{12}$cycloalkyl, phenyl; $R_{23}$ is H or Y—O—CO—O—$R_{22}$;

$R_{24}$ is H or CO—O—$R_{22}$;

T is OH or —OCO—CH=$CH_2$ or —OCO—C($CH_3$)=$CH_2$;

Y is $C_1$–$C_{12}$alkylene; $C_3$–$C_{12}$alkylene substituted by OH or $OR_{13}$; $C_4$–$C_{12}$alkylene interrupted by O; and T is linked to a primary carbon atom;

Z' is $C_1$–$C_{12}$alkylene; $C_2$–$C_{12}$alkylene interrupted by O; —O—($C_2$–$C_{12}$alkylene)—O—; —S—($C_2$–$C_{12}$alkylene)—S—;

Z" is $C_1$–$C_{12}$alkylene; $C_2$–$C_{12}$alkylene interrupted by O.

Compounds of the formula I' contain at least 2 highly reactive groups (linked directly to a phenyl ring and/or to an aliphatic substituent; see e.g. $R_2$, $R_3$, $R_{21}$), which groups are selected from OH or acrylic or methacrylic groups or aryl carbonate groups $OCOOR_{20}$, preferably at least 2 groups Y—T. Some compounds of specific interest contain 3 or more of these reactive groups; examples are compounds containing 2, 3 or 4 residues of the type Y—OH with aliphatic OH groups and/or Y—O—$COCHCH_2$, Y—O—COC($CH_3$)$CH_2$, $YOCOOR_{20}$ with $R_{20}$ being phenyl or naphthyl as defined above. Convenient examples for the highly reactive groups include 2-hydroxyethyl, 2-acryloxyethyl, 2-methacryloxyethyl, 2-(phenoxycarbonyl-oxy)ethyl. In compounds wherein R' is a group of formula II, those compounds are of specific interest wherein $R_6$ is H; OH; $C_1$–$C_4$alkyl; O—Y—T; $R_7$ is H; OH; $C_1$–$C_4$alkyl; $C_1$–$C_{12}$alkoxy; O—Y—T; or a group of the formula V. Preferred reactive groups are, for example, of the type Y—OH wherein OH bonds to $CH_2$ (primary carbon). In particularly preferred reactive groups —Y—T, Y is unbranched α,ω-bonded $C_2$–$C_{12}$alkylene, or said alkylene substituted or O—interrupted, where the term α,ω-bonded alkylene means that the 2 bonds are located on C atoms of both ends of the alkylene chain (primary carbon atoms); examples include $C_2$–$C_8$alkylenes such as 1,2-ethylene, 1,3-propylene, 1,4-butylene, 1,5-hexylene, 1,8-octylene.

Some compounds corresponding to formula I' of specific technical interest are those wherein R' is H, $C_1$–$C_{12}$alkyl; $C_5$–$C_{12}$cycloalkyl; $C_2$–$C_{18}$alkyl which is interrupted by one or more O; $SR_4$; $OR_5$; or is a group of formula II or III

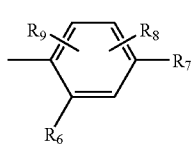

(II)

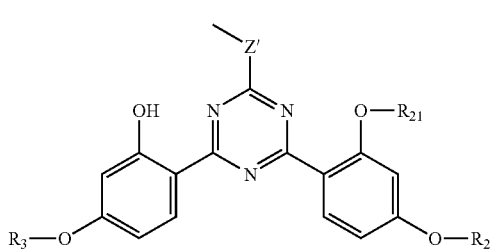

(III)

$R_2$, $R_{21}$ and $R_3$ independently of one another, are H or —Y—OH;

$R_4$ is $C_1$–$C_8$alkyl; or phenyl;

$R_5$ is $C_1$–$C_{12}$alkyl; $C_5$–$C_{12}$cycloalkyl; or $C_2$–$C_{18}$alkyl which is interrupted by one or more —O—;

$R_6$ is H; OH; $C_1$–$C_{12}$alkyl; $C_5$–$C_{12}$cycloalkyl; O—Y—OH;

$R_7$ is H; OH; $C_1$–$C_{12}$alkyl; $C_5$–$C_{12}$cycloalkyl; phenyl; $OR_{10}$; OCO—$R_{11}$; $NR_{12}$—CO—$R_{11}$; $SR_4$;

$R_8$ and $R_9$ independently are H or $C_1$–$C_{12}$alkyl;

$R_{10}$ is $C_1$–$C_{12}$alkyl; $C_2$–$C_{10}$alkenyl; Y—OH; or a group of the formula V

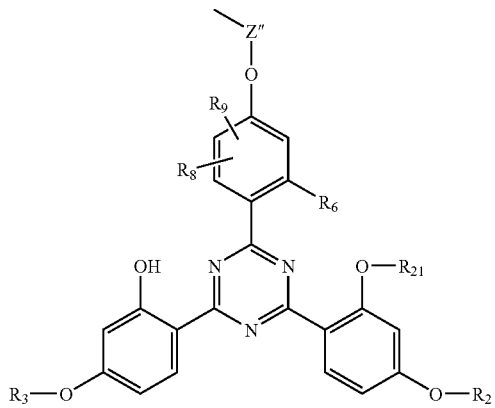

(V)

$R_{11}$ is $C_1$–$C_{12}$alkyl; $C_5$–$C_{12}$cycloalkyl; $C_2$–$C_6$alkenyl; $C_1$–$C_{12}$alkoxy;

$R_{12}$ is H; $C_1$–$C_{12}$alkyl; $C_5$–$C_{12}$cycloalkyl;

$R_{13}$ is $C_1$–$C_{18}$alkyl; phenyl; $C_7$–$C_{12}$alkylphenyl; benzyl;

Y is $C_1$–$C_{12}$alkylene; $C_3$–$C_{12}$alkylene substituted by OH or $OR_{13}$; $C_4$–$C_{12}$alkylene interrupted by O;

Z' is $C_1$–$C_{12}$alkylene; $C_2$–$C_{12}$alkylene interrupted by O; —O—($C_2$–$C_{12}$alkylene)—O—; —S—($C_2$–$C_{12}$alkylene)—S—;

Z" is $C_1$–$C_{12}$alkylene; $C_2$–$C_{12}$alkylene interrupted by O.

Preferred compounds of the formula I' are those wherein R' is a group of formula II

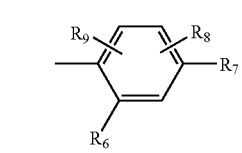

(II)

$R_2$, $R_{21}$ and $R_3$ independently of one another, are H or —Y—T;

$R_6$ is H; OH; $C_1$–$C_4$alkyl;

$R_7$ is H; OH; $C_1$–$C_4$alkyl; phenyl; $OR_{10}$;

$R_8$ is H, $C_1$–$C_{12}$alkyl or $C_7$–$C_{11}$phenylalkyl;

$R_9$ is H;

$R_{10}$ is $C_1$–$C_{12}$alkyl; Y—T; or a group of the formula V;

Y is $C_1$–$C_{12}$alkylene; $CH_2$—CH(OH)—$CH_2$; $CH_2$—CH($CH_2OR_{13}$)—; $C_4$–$C_{18}$alkylene interrupted by O.

More preferred is a process where in the compound of formula I'
R' is a group of formula II

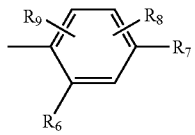

$R_2$ and $R_3$ independently of one another, are —Y—T;
$R_{21}$ is H or —Y—T;
$R_6$ is H; OH; methyl; or —OY—T; especially H; OH; or —OY—T;
$R_7$ is H; OH; methyl; phenyl; $OR_{10}$; especially H; OH; or $OR_{10}$;
$R_8$ and $R_9$ are H;
$R_{10}$ is $C_1$–$C_{12}$alkyl; or Y—T; especially $C_1$–$C_4$alkyl or $C_2$–$C_8$alkylene-T such as methyl or 2-hydroxyethyl;
T is OH or —OCO—CH=$CH_2$ or —OCO—C($CH_3$)=$CH_2$ or is $OCOOR_{20}$, wherein $R_{20}$ is phenyl or phenyl substituted by $C_1$–$C_8$alkyl;
Y is $C_2$–$C_{12}$alkylene; $CH_2$—CH(OH)—$CH_2$; $CH_2$—CH($CH_2OR_{13}$)—; especially $C_2$–$C_8$alkylene.

Some further compounds of preferred technical interest are those wherein each of $R_6$, $R_8$ and $R_9$ in formula (II) or (I') or (I") are H and $R_7$ is $C_1$–$C_{12}$alkoxy or O—YT, especially $C_1$–$C_4$alkoxy such as methoxy.

Within the process of the invention, compounds of the formula I' are effectively bonded to the polymeric material and immobilized therein. Surprisingly, the activity as UV absorber is effectively retained in the crosslinked state with low discoloration of the substrate.

Within the scope of the stated definitions, any alkyl groups such as the radicals R' or $R_4$ to $R_{10}$ as alkyl are branched or unbranched alkyl, for example methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl.

Aryl includes, for example, phenyl and naphthyl, preferably it is phenyl.

$R_8$ and $R_9$ include H, $C_1$–$C_{12}$alkyl and $C_7$–$C_{12}$phenylalkyl. Preferably, $R_8$ is located in 5-position and is H, alkyl such as propyl or butyl or pentyl or hexy or heptyl or octyl, or is phenylalkyl such as benzyl, α-methylbenzyl or α,α-dimethylbenzyl (cumyl). In compounds of specific technical interest, both $R_8$ and $R_9$ are H.

Residues $C_5$–$C_{12}$cycloalkyl comprise cyclopentyl, cyclohexyl, cycloheptyl, cyclooctyl, cyclononyl, cyclodecyl, cycloundecyl, cyclododecyl. Preference is given to cyclopentyl, cyclohexyl, cyclooctyl and cyclododecyl.

Residues alkenyl embrace, inter alia, vinyl, allyl, isopropenyl, 2-butenyl, 3-butenyl, isobutenyl, n-penta-2,4-dienyl, 3-methylbut-2-enyl, n-oct-2-enyl, n-dodec-2-enyl, isododecenyl, n-dodec-2-enyl or n-octadec-4-enyl. $R_{11}$ as alkenyl preferably is vinyl or 1-methylvinyl (isopropenyl).

Substituted alkyl, cycloalkyl or phenyl radicals can be substituted one or more times and can carry substituents on the bonding carbon atom (in α-position) or on other carbon atoms; if the substituent bonds by means of a heteroatom (for example alkoxy) it is preferably not in α-position and the substituted alkyl radical contains 2, especially 3, or more carbon atoms. Two or more substituents bond preferably to different carbon atoms.

Alkyl interrupted by —O— or —COO— (includes —OCO—) can be interrupted by one or more of these groups, one group in each case being inserted, in general into one bond. Hetero-hetero bonds, for example O—O, generally do not occure. If the interrupted alkyl is additionally substituted, the substituents are generally not α to the heteroatom.

$C_1$–$C_{20}$alkylene is, for example, methylene, ethylene, propylene, butylene, pentylene, hexylene, etc. The alkyl chain here can also be branched, as in isopropylene, for example.

O-interrupted alkylene is preferably derived from ethylene oxide and contains, within the definition given, one or more moieties of the formula ($CH_2$—$CH_2$—O). OH substituted alkylene is most preferably $CH_2$—CH(OH)—$CH_2$.

Preferably, the monomer, oligomer or polymer crosslinked by the instant process contains functional groups reactable with the compound of present formula I' selected from carboxylic, ester (including carbonate), amide, carbamate, anhydride, epoxy, isocyanate and/or reactive ethylenic double bonds.

Examples of polymer networks obtainable by the instant process, which are, at the same time, stabilized and/or made intransparent for UV radiation, are the following:
A. Polyurethanes derived from hydroxyl-functionalized polyethers, polyesters or polybutadienes on the one hand and aliphatic or aromatic polyisocyanates on the other, as well as precursors thereof.
B. Crosslinked polymers derived from aldehydes on the one hand and phenols, ureas and melamines on the other hand, such as phenol/formaldehyde resins, urea/formaldehyde resins and melamine/formaldehyde resins.
C. Unsaturated polyester resins derived from copolyesters of saturated and unsaturated dicarboxylic acids with polyhydric alcohols and vinyl compounds as crosslinking agents, and also halogen-containing modifications thereof of low flammability.
D. Hydroxy-functional acrylic resins on the one hand and melamines on the other hand.
E. Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or without accelerators.
F. Polyesters derived from dicarboxylic acids and diols and/or from hydroxycarboxylic acids or the corresponding lactones, for example polyethylene terephthalate (PET), polybutylene terephthalate, poly-1,4-dimethylolcyclohexane terephthalate, polyalkylene naphthalate (PAN) and polyhydroxybenzoates, as well as block copolyether esters derived from hydroxyl-terminated polyethers; and also polyesters modified with polycarbonates or MBS.
G. Polycarbonates and polyester carbonates, especially aromatic polycarbonates, for example those based on 2,2-bis(4-hydroxyphenyl)propane or 1,1-bis(4-hydroxyphenyl)cyclohexane.
H. Polyamides and copolyamides, for example those derived from diamines and dicarboxylic acids and/or from amino carboxylic acids or the corresponding lactams, such as polyamide 4, polyamide 6, polyamide 6/6, 6/10, 6/9, 6/12, 4/6, polyamide 11, polyamide 12, aromatic polyamides based on m-xylene, diamine and adipic acid; polyamides prepared from hexamethylenediamine and iso- and/or terephthalic acid with or without an elastomer as modifier, for example poly-2,4,4-trimethylhexamethyleneterephthalamide, poly-m-phenylene isophthalamide. Block copolymers of the abovementioned polyamides with polyolefins, olefin copolymers, ionomers or chemically bonded or grafted elastomers; or with polyethers, for example with polyethylene glycol, polypropylene glycol or polytetramethylene glycol. Furthermore, copolyamides or polyamides modified with EPDM or ABS; and polyamides which are condensed during processing (RIM polyamide systems).

In these systems, the component advantageously to be replaced, especially in part, by an aryl carbonate or especially hydroxy functional crosslinker of present formula I' is in A) hydroxyl-functionalized polyether, polyester or polybutadiene or its precursor;
B) phenol;
C) polyhydric alcohol (polyol);
D) hydroxy-functional acrylic resin;
E) epoxy phenol;
F) diol;
G) bisphenol;
H) diamine or diol.

Aryl carbonate functional crosslinkers of present formula I' are especially useful in polycarbonates (the above system G).

In case that only minor amounts (e.g. up to 5 mol-% of the conventional crosslinker) of the compound of present formula I' is to be incorporated, present compounds may be added to the formulation, which procedure results in competitive reaction of the compound of formula I' and the conventional crosslinker, and gives results comparable to those wherein the conventional crosslinker has been partly replaced.

Further systems curable according to the present invention are the following:
1. paints based on cold- or hot-crosslinkable alkyd, acrylate, polyester, epoxy or melamine resins or mixtures of such resins, if desired with addition of a curing catalyst;
2. two-component polyurethane paints based on hydroxyl-containing acrylate, polyester or polyether resins and aliphatic or aromatic isocyanates, isocyanurates or polyisocyanates;.
3. one-component polyurethane paints based on blocked isocyanates, isocyanurates or polyisocyanates which are deblocked-during baking, if desired with addition of a melamine resin;
4. one-component polyurethane paints based on a tris-alkoxycarbonyltriazine crosslinker and a hydroxyl group containing resin such as acrylate, polyester or polyether resins;
5. one-component polyurethane paints based on aliphatic or aromatic urethaneacrylates or polyurethaneacrylates having free amino groups within the urethane structure and melamine resins or polyether resins, if necessary with curing catalyst;
6. two-component paints based on (poly)ketimines and aliphatic or aromatic isocyanates, isocyanurates or polyisocyanates;
7. two-component paints based on (poly)ketimines and an unsaturated acrylate resin or a polyacetoacetate resin or a methacrylamidoglycolate methyl ester;
8. two-component paints based on carboxyl- or amino-containing polyacrylates and polyepoxides;
9. two-component paints based on acrylate resins containing anhydride groups and on a polyhydroxy or polyamino component;
10. two-component paints based on acrylate-containing anhydrides and polyepoxides;
11. two-component paints based on (poly)oxazolines and acrylate resins containing anhydride groups, or unsaturated acrylate resins, or aliphatic or aromatic isocyanates, isocyanurates or polyisocyanates;
12. two-component paints based on unsaturated polyacrylates and polymalonates;
13. thermoplastic polyacrylate paints based on thermoplastic acrylate resins or externally crosslinking acrylate resins in combination with etherified melamine resins;
14. paint systems based on siloxane-modified or fluorine-modified acrylate resins;
15. paint systems, especially for clearcoats, based on malonate-blocked isocyanates with melamine resins (e.g. hexamethoxymethylmelamine) as crosslinker (acid catalyzed);
16. UV-curable systems based on oligomeric urethane acrylates, or oligomeric urethane acrylates in combination with other oligomers or monomers;
17. dual cure systems, which are cured first by heat and subsequently by UV or electron irradiation, or vice versa, and whose components contain ethylenic double bonds capable to react on irradiation with UV light in presence of a photoinitiator or with an electron beam.

Crosslinking agents of present formula I' containing 2 types of reactive groups (e.g. reactive OH and reactive acrylate or methacrylate) are especially useful for dual cure systems such as those listed above. In these systems, the current crosslinkers react after heating with their hydroxyl function, and react upon irradiation with their (meth)acrylate function.

Monomers or oligomers usable in the process of the invention are all systems able to undergo a chemical bonding reaction with an aliphatic or aromatic OH, carbonate or acrylic functionality. These systems include polyepoxy, polyester as well as polyanhydride or UV curable type of coating binders; in these systems, the crosslinker of formula I' preferably contains T as OH and/or acryloxy or methacryloxy. Further systems are condensation polymers such as polyesters, polycarbonates, polyamides, or corresponding copolymers or blends; in these systems, the crosslinker of formula I' preferably contains T as OH and/or $OCOOR_{22}$. Among the latter, preference is given to the polycarbonates and polyesters. Polycarbonates are to be understood as meaning, in particular, those polymers whose constitutional repeating unit is of the formula —[O—A—O—CO]—, in which A is a divalent phenolic radical. Examples of A are given, inter alia, in U.S. Pat. No. 4,960,863 and in DE-A-39 22 496.

Thus, an embodiment of the invention is a process for the preparation of a polyester which comprises reacting one or more diacids with one or more diols in an esterification process, and/or one or more diesters with one or more diols in a transesterification process in the presence of an effective amount of a crosslinking agent of the formula I' or I''' containing at least 2 residues Y—OH.

Important monomers or oligomers reactive with a hydroxyfunctional crosslinking agent and to be used in the instant process are oligomeric or polymeric isocyanates, isocyanurates or melamines. Examples include commercially available isocyanates, e.g. Basonat® (BASF AG), Desmodur® (Bayer AG), Tolonate® (Rhodia Syntech GmbH, Germany) etc., as well as melamines, e.g. Setamine® (Akzo Nobel Resins BV), Cymel® (Cytec Industries Inc.), Maprenal® (Vianova Resins GmbH).

Crosslinking agents of present formula I' containing reactive acrylate and/or methacrylate are especially useful for radiation-curable coating compositions. In this case, the binder essentially comprises monomeric or oligomeric compounds containing ethylenically unsaturated bonds (prepolymers), which after application are cured by actinic radiation, i.e. converted into a crosslinked, high molecular weight form. Where the system is UV-curing, it generally contains at least one photoinitiator as well. Corresponding systems are described in the abovementioned publication Ullmann's Encyclopedia of Industrial Chemistry, 5th Edition, Vol. A18, pages 451–453.

The coating compositions according to the invention can be applied to any desired substrates, for example to metal, wood, plastic or ceramic materials. They are preferably used as topcoat in the finishing of automobiles. If the topcoat comprises two layers, of which the lower layer is pigmented and the upper layer is not pigmented, the novel coating composition can be used for either the upper or the lower layer or for both layers, but preferably for the upper layer.

The novel coating compositions can be applied to the substrates by the customary methods, for example by brushing, spraying, pouring, dipping or electrophoresis; see also Ullmann's Encyclopedia of Industrial Chemistry, 5th Edition, Vol. A18, pp. 491–500.

Addition of the present stabilizer to a pigmented coating may also protect the pigment from damaging effects of UV radiation, especially in the case of liquid crystal pigments.

Products of the present process find utility mainly as coatings or as printing plates or as transparent UV shielding such as transparent packaging container or film. Other components useful in these fields are, for example, as described in WO 01/47900, pages 32–41 and publications cited therein, for coating systems, or Ullmann's Encyclopedia of Industrial Chemistry, $6^{th}$ Edn, 1999 Electronic Release, section Imaging Technology 3.4., or in U.S. Pat. No. 4,868,091 or EP-A-485334 for printing plates, especially letterpress and flexographic plates.

In the case of flexographic printing plates, the crosslinked product of the invention may be any layer, e.g. the photopolymer layer or the base material or, if present, the adhesive, release layer or protective layer.

Coatings containing the crosslinked product of the invention may be mono- or multilayer coatings such as automobile coatings or coilcoats. In case of multilayer coatings like automobile coatings, the product of the invention may be or be part of the base coat, color coat and/or, if present, the clearcoat. Preferred is the use of the product of present process as topcoat for automobiles.

The invention therefore also pertains to a coating, e.g. automobile or coil coating, which coating comprises the reaction product of a compound of the formula I' and a binder resin capable of reacting with hydroxyl groups.

The invention further pertains to a printing plate, e.g. a flexographic printing plate, comprising the reaction product of a compound of the formula I' and a binder resin capable of reacting with hydroxyl groups.

Especially in flexographic printing plates, the homogenous and stable concentration of the UV absorber is of high importance in order to effectively absorb scattered light across the plate. Thickness of these plates usually is between 0.5 and 10 mm, especially from 0.7 to 7 mm.

The crosslinker/stabilizer of the invention can be an individual compound of the formula I' or else a mixture.

In the instant process, the compounds of the formula I' may be used as the sole crosslinker or, preferably, other known crosslinkers, preferably acrylate- or methacrylate or hydroxyfunctional or thiol-functional ones, may be used concomitantly. Examples for hydroxy- and thiol-functional crosslinkers are polyols and thiols, such as:

Aromatic and especially aliphatic and cycloaliphatic polyols. Examples of aromatic polyols are hydroquinone, 4,4'-dihydroxydiphenyl, 2,2-di(4-hydroxyphenyl)propane, and novolaks and resoles. Examples of polyepoxides are those based on the said polyols, especially the aromatic polyols and epichlorohydrin. Also suitable as polyols are polymers and copolymers that contain hydroxyl groups in the polymer chain or in side groups, e.g. polyvinyl alcohol and copolymers thereof or polymethacrylic acid hydroxyalkyl esters or copolymers thereof. Further suitable polyols are oligoesters having hydroxyl terminal groups.

Examples of aliphatic and cycloaliphatic polyols include alkylenediols having preferably from 2 to 12 carbon atoms, such as ethylene glycol, 1,2- or 1,3-propanediol, 1,2-, 1,3- or 1,4-butanediol, pentanediol, hexanediol, octanediol, dodecanediol, diethylene glycol, triethylene glycol, polyethylene glycols having molecular weights of preferably from 200 to 1500, 1,3-cyclopentanediol, 1,2-, 1,3- or 1,4-cyclohexanediol, 1,4-dihydroxymethylcyclohexane, glycerol, tris(,-hydroxy-ethyl)amine, trimethylolethane, trimethylolpropane, pentaerythritol, dipenta-erythritol and sorbitol.

The polyols may be partially or fully esterified by one or by different unsaturated carboxylic acid(s), it being possible for the free hydroxyl groups in partial esters to be modified, for example etherified, or esterified by other carboxylic acids.

Commercially available materials include Sentalux® (Akzo Nobel Resins BV), Desmophen® (Bayer AG), Macrynal® (Vianova Resins GmbH), Viacryl® (Vianova Resins GmbH).

In the preferred process of the invention, a fraction of the conventional crosslinker is replaced by the compound of formula I'.

Preferably 0.01 to 50%, more preferably 0.1 to 20%, especially 0.5 to 10% by weight of the polyol or polyol equivalent component in the crosslinkable system are replaced by the compound of present formula I', corresponding to a preferred weight ratio of 1 part by weight of the compound of formula I' on 1 to approximately 1000, more preferably 1 on 4 to 200, especially 1 on 9 to 200 parts by weight of polyol or polyol equivalent component.

The amount of crosslinker/stabilizer of the invention to be used depends on the specific polymer and on the intended use of the crosslinked material. In a preferred embodiment, the process comprises addition of a compound of the formula I' in an amount from 0.01 to 25, especially from 0.05 to 15 and, in particular, from 0.1 to 10 parts by weight per 100 parts by weight of monomer and/or oligomer to be crosslinked.

Advantageously, compounds of the formula I' are added to a binder, e.g. a polyisocyanate or polyisocyanurate, before or at the same time as the conventional crosslinker, e.g. polyol or polysulphide.

Depending on the polymer system, crosslinking can be achieved by heating e.g. to 50–400° C., e.g. to 50–150° C. in case of OH or (meth)acrylic functionality in the UV absorber of formula I' and a polymer system selected from typical coating binders such as those listed above under A–E and 1–17; or up to 400° C. for polycarbonates, polyamides or polyesters such as those listed above under F, G and H, or corresponding blends or copolymers. Preferably, the present process is carried out in the temperature range from about 20° above the glass transition temperature (or melting point in case of a crystalline polymer) to about 300° C. in case of a polyester, 340° C. in case of a polyamide and 360° C. in case of a polycarbonate.

A fully crosslinked system is obtained, whereby the UV absorber of present formula I' is fully built into the system. Substantially no UV absorber is lost by migration or extraction. Sometimes temperatures up to 300° C. are reached during the preparation of crosslinked systems, whereupon non-fixed UV absorbers are lost by evaporation.

Components used in the instant process such as crosslinkable monomers and/or oligomers and hydroxyfunctional or thiohydroxyfunctional crosslinkers are known in the art and largely items of commerce, e.g. in the coatings industry.

Compounds of the formula I' can be obtained in analogy to known compounds by common methods, for example in accordance with or in analogy to one of the methods given in GB-A-975966; U.S. Pat. No. 3,244,708; CH-A-484695; U.S. Pat. No. 4,826,978; EP-A-434 608 or in the publication by H. Brunetti and C. E. Lüthi, Helv. Chim. Acta 55, 1566 (1972). Further details on starting compounds which can be used and on their preparation can be found in the literature cited at the outset and in EP-A-165 608.

Introduction of a hydroxy containing substituent —Y—OH can, for example, be achieved by reacting an appropriate bis-resorcinyl triazine

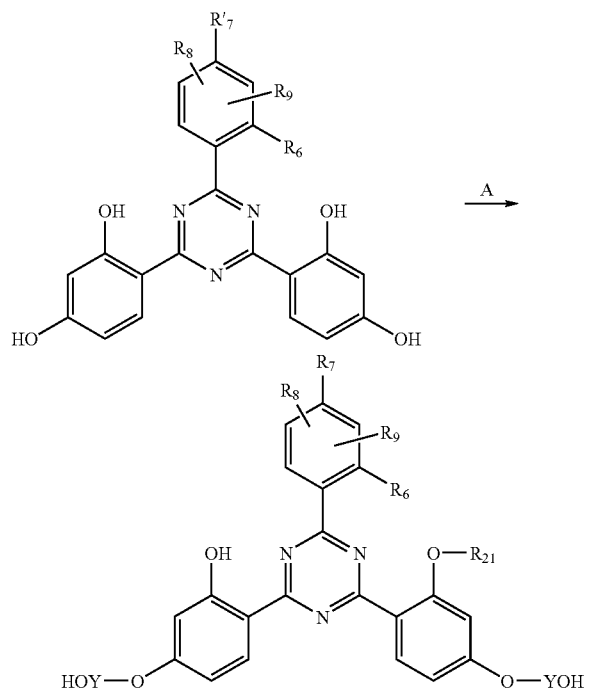

wherein Y, $R_{21}$, $R_6$, $R_7$, $R_8$ and $R_9$ are as defined above, and $R'_7$ is H; OH; $C_1$–$C_{12}$alkyl; $C_5$–$C_{12}$cycloalkyl; phenyl; OCO—$R_{11}$; $NR_{12}$—CO—$R_{11}$; $SR_4$;

with reagent A, which may be Br—Y—OH, or a suitable epoxide or cyclic carbonate ester like ethylene oxide or

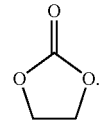

Other compounds of formula I', e.g. those wherein R' is H, $C_1$–$C_{12}$alkyl; $C_5$–$C_{12}$cycloalkyl; $C_2$–$C_{18}$alkyl which is interrupted by one or more O; $SR_4$; $OR_5$; or is a group of formula III, may be obtained in an analogous manner from suitable precursors.

In addition to the compounds of the formula I', the instant polymer compositions may comprise before and after crosslinking as additional component one or more customary additives, for example antioxidants, other light stabilizers, metal passivators. Examples of these are the following:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl) adipate.

1.4. Tocopherols, for example α-tocopherol, β-tocopherol, γ-tocopherol, δ-tocopherol and mixtures thereof (Vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis(2,6-dimethyl-4-hydroxyphenyl)disulfide.

1.6. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl- 5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis-(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra-(5-tert-butyl-4-hydroxy-2-methylphenyl) pentane.

1.7. O-, N- and S-benzyl compounds, for example 3,5,3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5-di-tert-butyl-4-hydroxybenzylmercaptoacetate.

1.8. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, di-dodecylmercaptoethyl-2,2-bis-(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl)malonate.

1.9. Aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine Compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris-(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl) propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15. Esters of β-(3,5-dicyclohexyl-4-hydroxyphenyl)propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene, glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo [2.2.2]octane.

1.17. Amides of β-(3-(3,5-di-tert-butyl-4-hydroxyphenyl) propionic acid e.g. N,N'-bis(3,5-di-tert-butyl-4-hydroxyphenylpropionyl)hexamethylenediamide, N,N'-bis(3,5-di-tert-butyl-4-hydroxyphenylpropionyl) trimethylenediamide, N,N'-bis(3,5-di-tert-butyl-4-hydroxyphenylpropionyl)hydrazide, N,N'-bis[2-(3-[3,5-di-tert-butyl-4-hydroxyphenyl]propionyloxy)ethyl] oxamide (Naugard®XL-1 supplied by Uniroyal).

1.18. Ascorbic Acid (Vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclo-hexyl-N'-phenyl-p-phenlenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxy-diphenylamine, N-phenyl-1-naphthylamine, N-(4-tert-octylphenyl)-1-naphthylamine, N-phenyl-2-naphthylamine, octylated diphenylamine, for example p,p'-di-tert-octyl-diphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4, 4'-diaminodiphenylmethane, 1,2-bis[(2-methylphenyl) amino]ethane, 1,2-bis(phenylamino)propane, (o-tolyl) biguanide, bis[4-(1',3'-dimethylbutyl)phenyl]amine, tertoctylated N-phenyl-1-naphthylamine, a mixture of mono- and dialkylated tert-butyl/tert-octyidiphenylamines, a mixture of mono- and dialkylated nonyidiphenylamines, a mixture of mono- and dialkylated dodecyldiphenylamines, a mixture of mono- and dialkylated isopropyl/isohexyldiphenylamines, a mixture of mono- und dialkylated tert-butyldiphenylamines, 2,3-dihydro-3,3-dimethyl-4H-1,4-benzothiazine, phenothiazine, a mixture of mono- und dialkylated tert-butyl/tert-octylphenothiazines, a mixture of mono- und dialkylated tert-octyl-phenothiazines, N-allylphenothiazin, N,N,N',N'-tetraphenyl-1,4-diaminobut-2-ene, N,N-bis(2,2,6,6-tetramethyl-piperid-4-yl-hexamethylenediamine, bis(2,2,6,6-tetramethylpiperid-4-yl)sebacate, 2,2,6,6-tetramethylpiperidin-4-one, 2,2,6,6-tetramethylpiperidin-4-ol.

2. UV Absorbers and Light Stabilisers 2.1. 2-(2'-Hydroxyphenyl)benzotriazoles, for example 2-(2'-hydroxy-5'-methylphenyl)-benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis-(α,α-dimethylbenzyl)-2'-hydroxyphenyl)benzotriazole, 2-(3'-tert-butyl-2'-hydroxy-5'-(2-octyloxycarbonylethyl) phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl) phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, 2-(3'-tert-butyl-2'-hydroxy-5'-(2-isooctyloxycarbonylethyl) phenylbenzotriazole, 2,2'-methylene-bis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; R—CH$_2$CH$_2$—COO—CH$_2$CH$_2$$]_2$ where R=3'-tert-butyl-4'-hydroxy-5'-2H-benzotriazol-2-ylphenyl, 2-[2'-hydroxy-3'-(α,α-dimethylbenzyl)-5'-(1,1,3,3-tetramethylbutyl)-phenyl]benzotriazole; 2-[2'-hydroxy-3'-(1,1,3,3-tetramethylbutyl)-5'-(α,α-dimethylbenzyl)-phenyl]benzotriazole.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutyl-phenyl salicylate, phenyl salicylate, octylphenyl salicylate, dibenzoyl resorcinol, bis(4-tert-butylbenzoyl) resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxy-cinnamate, butyl α-cyano-β-methyl-p-methoxy-cinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyidithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amines, for example bis(2,2,6,6-tetramethyl-4-piperidyl)sebacate, bis(2,2,6,6-tetramethyl-4-piperidyl)succinate, bis(1,2,2,6,6-pentamethyl-4-piperidyl)sebacate, bis(1-octyloxy-2,2,6,6-tetramethyl-4-piperidyl)sebacate, bis(1,2,2,6,6-pentamethyl-4-piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl)nitrilotriacetate, tetrakis(2,2,6,6-tetramethyl-4-piperidyl)-1,2,3,4-butane-tetracarboxylate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decan-2,4-dione, bis(1-octyloxy-2,2,6,6-tetramethylpiperidyl)sebacate, bis(1-octyloxy-2,2,6,6-tetramethylpiperidyl)succinate, linear or cyclic condensates of N,N'-bis-(2,2,6,6-tetramethyl-4-piperidyl) hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidin-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensation product of N,N'-bis(2,2,6,6-tetramethyl-4-piperidyl) hexamethylenediamine and 4-cyclohexylamino-2,6-dichloro-1,3,5-triazine, a condensation product of 1,2-bis (3-aminopropylamino)ethane and 2,4,6-trichloro-1,3,5-triazine as well as 4-butylamino-2,2,6,6-tetramethylpiperidine (CAS Reg. No. [136504-96-6]); N-(2,2,6,6-tetramethyl-4-piperidyl)-n-dodecylsuccinimid, N-(1,2,2,6,6-pentamethyl-4-piperidyl)-n-dodecylsuccinimid, 2-undecyl-7,7,9,9-tetramethyl-1-oxa-3,8-diaza-4-oxo-spiro[4,5]decane, a reaction product of 7,7,9,9-tetramethyl-2-cycloundecyl-1-oxa-3,8-diaza-4-oxospiro [4,5]decane und epichlorohydrin, 1,1-bis(1,2,2,6,6-pentamethyl-4-piperidyloxycarbonyl)-2-(4-methoxyphenyl)ethene, N,N'-bis-formyl-N,N'-bis(2,2,6,6-tetramethyl-4-piperidyl)hexamethylenediamine, diester of 4-me-thoxy-methylene-malonic acid with 1,2,2,6,6-pentamethyl-4-hydroxypiperidine, poly[methylpropyl-3-oxy-4-(2,2,6,6-tetramethyl-4-piperidyl)]siloxane, reaction product of maleic acid anhydride-α-olefin-copolymer with 2,2,6,6-tetramethyl-4-aminopiperidine or 1,2,2,6,6-pentamethyl-4-aminopiperidine, the reaction product of 2,4-bis[(1-cyclohexyloxy-2,2,6,6-piperidin-4-yl)butylamino]-6-chloro-s-triazine with N,N'-bis(3-aminopropyl)ethylenediamine), 5-(2-ethylhexanoyl)-oxymethyl-3,3,5-trimethyl-2-morpholinone, 1-(2-hydroxy-2-methylpropoxy)-4-octadecanoyloxy-2,2,6,6-tetramethylpiperidine, 1,3,5-tris(N-cyclohexyl-N-(2,2,6,6-tetramethylpiperazin-3-on-4-yl)amino)-s-triazine, 1,3,5-tris(N-cyclohexyl-N-(1,2,2,6,6-pentamethylpiperazin-3-on-4-yl)amino)-s-triazine.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxy-propoxy)phenyl]-4,6-bis(2,4-dimethyl)-1,3,5-triazine, 2-[2-hydroxy-4-(2-hydroxy-3-octyloxy-propyloxy)phenyl]-4,6-bis(2,4-dimethyl)-1,3,5-triazine, 2-[4-(dodecyloxy/tridecyloxy-2-hydroxypropoxy)-2-hydroxy-phenyl]-4,6-bis(2,4-dimethylphenyl)-1,3,5-triazine, 2-[2-hydroxy-4-(2-hydroxy-3-dodecyloxy-propoxy)phenyl]-4,6-bis(2,4-dimethylphenyl)-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxy-propoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxy-propoxy]phenyl}-4,6-bis(2,4-dimethylphenyl)-1,3,5-triazine, 2-(2-hydroxy-4-(2-ethylhexyl)oxy)phenyl-4,6-di(4-phenyl)phenyl-1,3,5-triazine, 2-(2-hydroxy-4-(1-octyloxycarbonylethoxy)phenyl-4,6-di(4-phenyl-phenyl)-1,3,5-triazine, 2,4-diphenyl-6-(2-hydroxy-4-(2-(2-ethylhexanoyloxy)ethoxy)-phenyl)-1,3,5-triazine, 2,4-bis-(4-[2-ethylhexyloxy]-2-hydroxyphenyl)-6-(4-methoxyphenyl)-1,3,5-triazine, the reaction product of 1 mol of tris(2,4-dihydroxyphenyl)-1,3,5-triazine with 2–4 mol of am ester mixture of straight and branched chain $C_7$, $C_8$ and $C_9$ alcohols and bromopropionic acid.

3. Metal deactivators, for example N,N'-diphenyloxamide, N-salicylal-N'-salicyloyl hydrazine, N,N'-bis(salicyloyl) hydrazine, N,N'-bis(3,5-di-tert-butyl-4-hydroxyphenylpropionyl) hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl)-pentaerythritol diphosphite, diisodecyloxypentaerythritol diphosphite, bis(2,4-di-tert-butyl-6-methylphenyl)pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, 6-fluoro-2,4,8,10-tetra-tert-butyl-12-methyl-dibenz[d,g]-1,3,2-dioxaphosphocin, bis(2,4-di-tert-butyl-6-methylphenyl) methyl phosphite, bis(2,4-di-tert-butyl-6-methylphenyl) ethyl phosphite, 2,2',2"-nitrilo[triethyltris(3,3',5,5'-tetra-tert-butyl-1,1'-biphenyl-2,2'-diyl)phosphite], 2-ethylhexyl(3,3',5,5'-tetra-tert-butyl-1,1'-biphenyl-2,2'-di-yl)phosphite.

Especially preferred are the following phosphites:

Tris(2,4-di-tert-butylphenyl) phosphite (Irgafos®168, Ciba-Geigy), tris(nonylphenyl) phosphite,

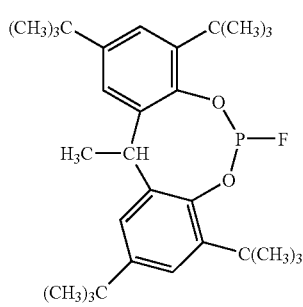

(A)

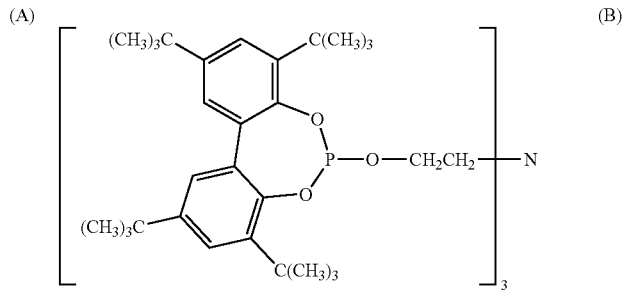

(B)

-continued

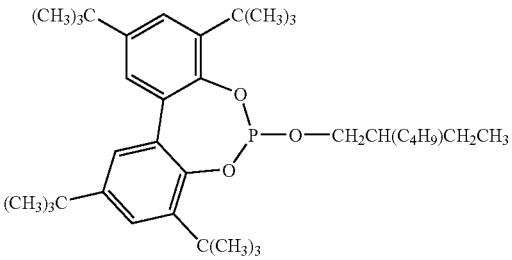
(C)

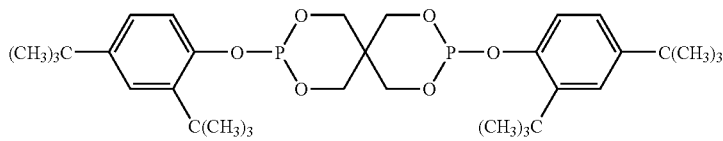
(D)

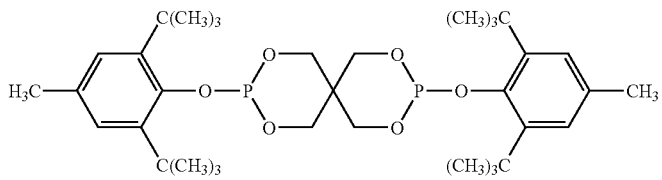
(E)

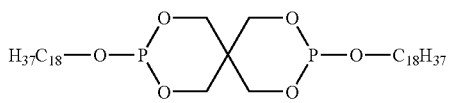
(F)

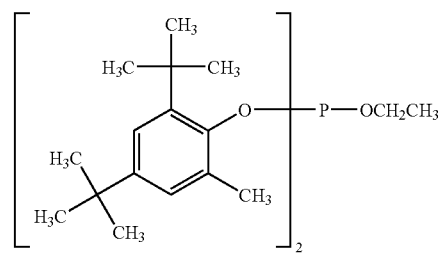
(G)

5. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

6. Nitrones, for example, N-benzyl-alpha-phenyl-nitrone, N-ethyl-alpha-methyl-nitrone, N-octyl-alpha-heptyl-nitrone, N-lauryl-alpha-undecyl-nitrone, N-tetradecyl-alpha-tridcyl-nitrone, N-hexadecyl-alpha-pentadecyl-nitrone, N-octadecyl-alpha-heptadecyl-nitrone, N-hexadecyl-alpha-heptadecyl-nitrone, N-ocatadecyl-alpha-pentadecyl-nitrone, N-heptadecyl-alpha-heptadecyl-nitrone, N-octadecyl-alpha-hexadecyl-nitrone, nitrone derived from N,N-dialkylhydroxylamine derived from hydrogenated tallow amine.

7. Thiosynergists, for example, dilauryl thiodipropionate or distearyl thiodipropionate.

8. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyidithiocarbamate, dioctadecyl disulfide, pentaerythritol tetrakis(β-dodecylmercapto)propionate.

9. Polyamide stabilisers, for example, copper salts in combination with iodides and/or phosphorus compounds and salts of divalent manganese.

10. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or zink pyrocatecholate.

11. Nucleating agents, for example, inorganic substances such as talcum, metal oxides such as titanium dioxide or magnesium oxide, phosphates, carbonates or sulfates of, preferably, alkaline earth metals; organic compounds such as mono- or polycarboxylic acids and the salts thereof, e.g. 4-tert-butylbenzoic acid, adipic acid, diphenylacetic acid, sodium succinate or sodium benzoate; polymeric compounds such as ionic copolymers (ionomers).

12. Fillers and reinforcing agents, for example, calcium carbonate, silicates, glass fibres, glass beads, asbestos, talc, kaolin, mica, barium sulfate, metal oxides and hydroxides, carbon black, graphite, wood flour and flours or fibers of other natural products, synthetic fibers.

13. Other additives, for example, plasticisers, lubricants, emulsifiers, pigments, rheology additives, catalysts, flow-control agents, optical brighteners, flameproofing agents, antistatic agents, clarifiers such as substituted and unsubstituted bisbenzylidene sorbitols, benzoxazinone UV absorbers such as 2,2'-p-phenylene-bis(3,1-benzoxazin-4-one), Cyasorb® 3638 (CAS# 18600-59-4), and blowing agents.

14. Benzofuranones and indolinones, for example those disclosed in U.S. Pat. No. 4,325,863; U.S. Pat. No. 4,338,244; U.S. Pat. No. 5,175,312; U.S. Pat. No. 5,216,052; U.S. Pat. No. 5,252,643; DE-A-4316611; DE-A-4316622; DE-A-4316876; EP-A-0589839 or EP-A-0591102 or 3-[4-(2-acetoxyethoxy)phenyl]-5,7-di-tert-butyl-benzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]phenyl) benzofuran-2-one], 5,7-di-tert-butyl-3-(4-ethoxyphenyl) benzofuran-2-one, 3-(4-acetoxy-3,5-dimethylphenyl)-5,7-di-tert-but-yl-benzofuran-2-one, 3-(3,5-dimethyl-4-pivaloyloxyphenyl)-5,7-di-tert-butyl-benzofuran-2-one, 3-(3,4-dimethylphenyl)-5,7-di-tert-butyl-benzofuran-2-one, 3-(2,3-dimethylphenyl)-5,7-di-tert-butyl-benzofuran-2-one.

15. Dispersing Agents, such as polyethylene oxide waxes or mineral oil.

The nature and amount of the further stabilizers added are determined by the nature of the substrate to be stabilized and by its intended use. It is common to employ 0.1–10, for example 0.2–5% by weight, based on the material to be stabilized.

It is particularly advantageous to employ the novel compounds in combination with a light stabilizer of the sterically hindered amine type, the 2-(2-hydroxyphenyl)-1,3,5-triazine and/or 2-hydroxyphenyl-2H-benzotriazole type, for example as mentioned in the above list in sections 2.1, 2.6 and 2.8. Further examples for light stabilizers of the 2-(2-hydroxyphenyl)-1,3,5-triazine type advantageously to be added can be found e.g. in the publications U.S. Pat. No. 4,619,956, EP-A-434608, U.S. Pat. No. 5,198,498, U.S. Pat. No. 5,322,868, U.S. Pat. No. 5,369,140, U.S. Pat. No. 5,298,067, WO-94/18278, EP-A-704437, GB-A-2297091, WO-96/28431. Of special technical interest is the addition of the 2-(2-hydroxyphenyl)-1,3,5-triazines and/or 2-hydroxyphenyl-2H-benzotriazoles, especially the 2-(2-hydroxyphenyl)-1,3,5-triazines selected from 2-resorcinyl-4,6-bis(biphenylyl)-1,3,5-triazines. Of major importance are sterically hindered amines, for example those indicated in the list above under 2.6 or those selected from 2,2,6,6-tetraalkylpiperidine and/or 3,3,5,5-tetraalkyl-morpholin-2-one derivatives which comprise at least one group of the formula

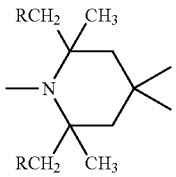 and/or 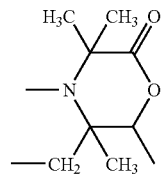

in which R is hydrogen or methyl, especially hydrogen.

Examples of tetraalkylpiperidine derivatives which can be used as component C are given in EP-A-356 677, pages 3–17, sections a) to f). These sections of this EP-A are considered as part of the present description. It is particularly judicious to employ the following tetraalkylpiperidine derivatives:

bis-(2,2,6,6-tetramethylpiperidin-4-yl) succinate,
bis-(2,2,6,6-tetramethylpiperidin-4-yl) sebacate,
bis-(1,2,2,6,6-pentamethylpiperidin-4-yl) sebacate,
di(1,2,2,6,6-pentamethylpiperidin-4-yl) butyl(3,5-di-tert-butyl-4-hydroxy-benzyl)malonate,
bis-(1-octyloxy-2,2,6,6-tetramethylpiperidin-4-yl) sebacate,
tetra(2,2,6,6-tetramethylpiperidin-4-yl) butane-1,2,3,4-tetracarboxylate,
tetra(1,2,2,6,6-pentamethylpiperidin-4-yl) butane-1,2,3,4-tetracarboxylate,
2,2,4,4-tetramethyl-7-oxa-3,20-diaza-21-oxodispiro[5.1.11.2]heneicosane,
8-acetyl-3-dodecyl-1,3,8-triaza-7,7,9,9-tetramethylspiro[4.5]decane-2,4-dione,
1,1-bis(1,2,2,6,6-pentamethylpiperidin-4-yl-oxycarbonyl)-2-(4-methoxyphenyl)-ethene,
5-(2-ethylhexanoyl)-oxymethyl-3,3,5-trimethyl-2-morpholinone,
1-(2-hydroxy-2-methylpropoxy)-4-octadecanoyloxy-2,2,6,6-tetramethypiperidine, or a compound of the formulae

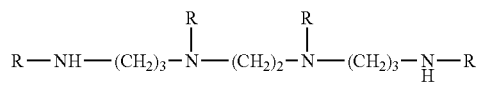

where R =

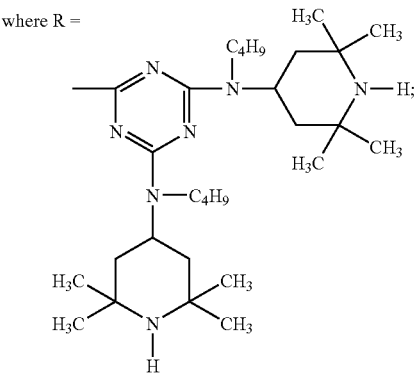

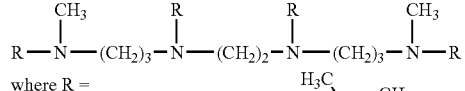

where R =

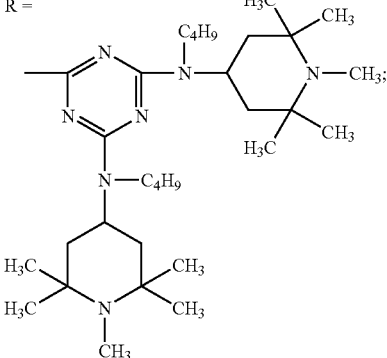

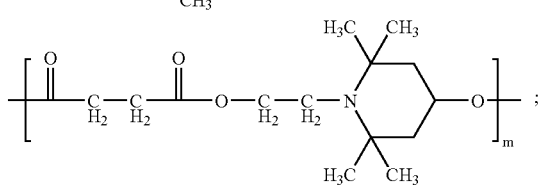

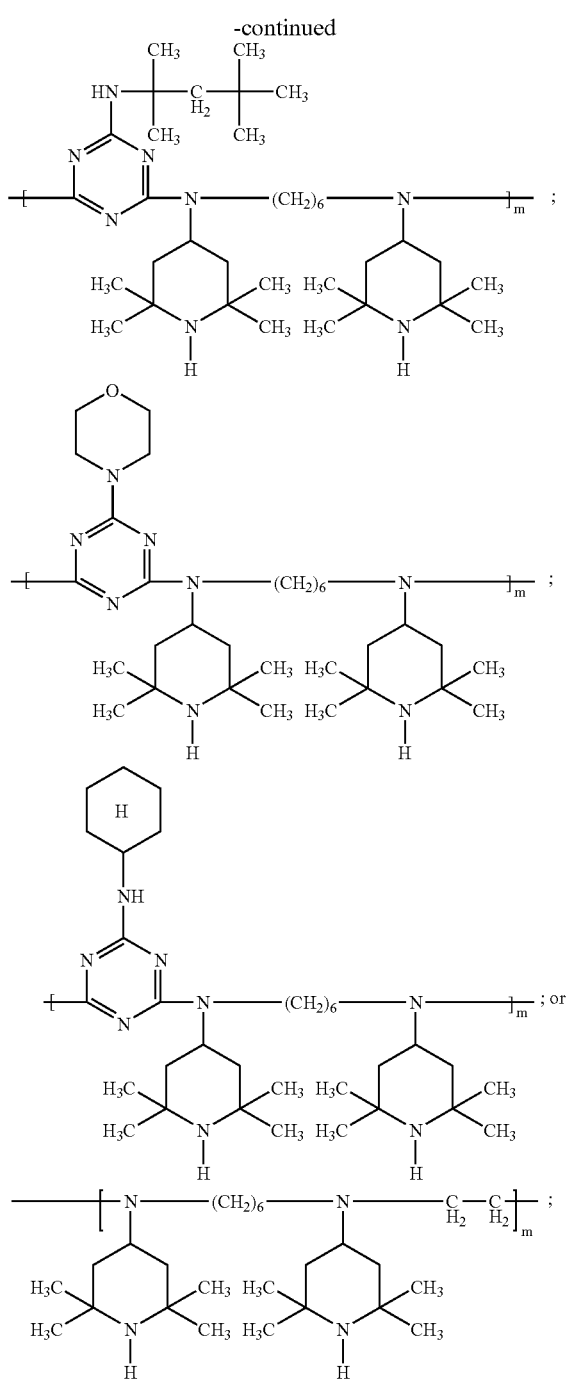

where m is 5–50.

In addition, the instant crosslinkable composition as well as the crosslinked polymer may also comprise further components, for example solvents, pigments, dyes, plasticizers, stabilizers, thixotropic agents, drying catalysts and/or levelling agents.

Examples of possible components are those as descibred in Ullmann's Encyclopedia of Industrial Chemistry, 5th ed., Vol. A18, pp. 429–471, VCH, Weinheim 1991.

The novel crosslinkable compositions can be applied to any desired substrates, for example to metal, wood, plastic or ceramic materials. Application may follow customary techniques, for example by spreading, spraying, flow coating, brushing, rolling, dipping or electrophoresis; see also Ullmann's Encyclopedia of Industrial Chemistry, 5th ed., Vol.A18, pp. 491–500.

The coatings obtained in accordance with the invention possess an outstanding resistance to the damaging effects of light, oxygen and heat; particular mention should be made of the good light stability and weathering stability of the resulting coatings, for example paints.

The invention therefore also provides a coating, especially a paint, which is stabilized against the damaging effects of light, oxygen and heat by the addition of a compound of the formula I' and crosslinking. The paint is preferably a topcoat for automobiles. The invention in addition comprises a process for crosslinking and stabilizing a coating based on organic polymers against damage by light, oxygen and/or heat, which comprises incorporating a compound of the formula I', and provides for the use of compounds of the formula I' in coating compositions as crosslinkers and stabilizers against damage by light, oxygen and/or heat.

The coating compositions can comprise an organic solvent or solvent mixture in which the binder is soluble. The coating composition can also be an aqueous solution or dispersion, however. The vehicle can also be a mixture of an organic solvent and water. The coating composition may also be a high-solids system or can be solvent-free (for example powder coating). Powder coatings are those, for example, as described in Ullmann's Encyclopedia of Industrial Chemistry, 5th ed., A18, pages 438–444. The powder coating can also be in the form of a powder slurry, i.e. a dispersion of the powder in—preferably—water.

The pigments can be inorganic, organic or metallic pigments. The novel coating compositions preferably contain no pigments and are used as clearcoat. Likewise preferred is the use of the coating composition as a topcoat for applications in the automotive industry, especially as a pigmented or unpigmented top layer of the coating system. Its use for underlying coats, however, is also possible.

Incorporation into the organic material to be stabilized/crosslinked can take place, for example, by mixing or applying the compounds of the formula I' and any other additives by methods customary in the art. The reactive crosslinkers of the formula I' may be added before or during the polymerization step, before or during crosslinking, or to the polymer. Where the materials are oligo/polymers, especially synthetic, incorporation preferably takees place prior to crosslinking. If the process of the invention is carried out by reacting a polymer with the crosslinker of present formula 1', the reaction may take place during melt processing of the polymer, for example at a temperature in the range 50–350° C. When the process is run as a reactive extrusion, the processing machine, e.g. extruder or kneader, preferably is equipped with at least one vent zone to which underpressure may be applied.

The invention therefore further pertains to a process wherein the monomer, oligomer and/or polymer is selected polyesters, copolyesters or polyester blends by adding one or more than one compounds of the formula I' to the processing apparatus and fusing the mixture to above the melting point, in which process the processing apparatus is a single-screw extruder, twin-screw extruder, planetary-gear extruder, ring extruder or Ko-kneader having at least one vent zone to which underpressure is applied.

The compounds of the formula I' can judiciously be incorporated by the following methods:
as an emulsion or dispersion (e.g. to latices or emulsion polymers),
as a dry mix during the mixing in of additional components or polymer mixtures,
by direct addition to the processing apparatus (e.g. extruders, internal mixers etc.)
as a solution or melt.

Equipment, reaction conditions as well as monomer, oligomer or polymer components for the condensation reaction, especially with a crosslinker of present formula I' wherein T is OH or $OCOOR_{22}$, may be of the type described in U.S. Pat. No. 5,859,073 (see, for example, polyester and polycarbonate components and preparation methods thereof listed from col. 1, line 49, to col. 5, line 64), U.S. Pat. No. 6,265,533 (see, for example, melt processing conditions and equipment described in col. 2, lines 1–48 [temperature range in line 40 should read as "180 to 320° C."], and in the examples [col. 18, line 49, to col. 20, line 56]), or U.S. Pat. No. 6,469,078 (see, for example, polycondensates, precursors thereof and blends listed from col. 3, line 1, to col. 7, line 5), the corresponding passages of which are herby incorporated by reference.

The present crosslinker of formula I' may also be employed for increasing the molecular weight of condensation polymers, e.g. polyesters or polycarbonates, in the way described in U.S. Pat. No. 6,469,078.

The stabilized polymer compositions obtained in this way can also be used for the production of shaped articles, for example fibres, films, tapes, sheets, sandwich boards, vessels, pipes and other profiles, by methods customary in the art.

compounds of the formula I' and I" are novel. Thus, the invention also pertains to a compound of the formula I' or I" as described above.

Preferred among these novel compounds are those of the formula

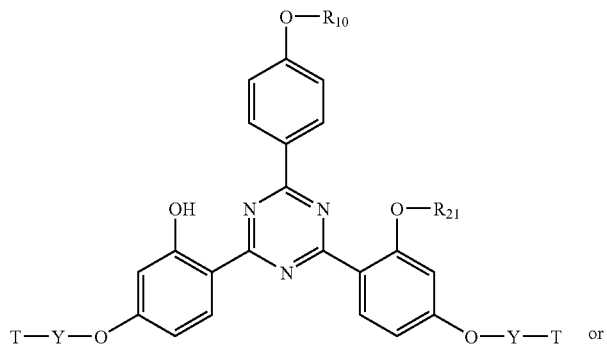

or

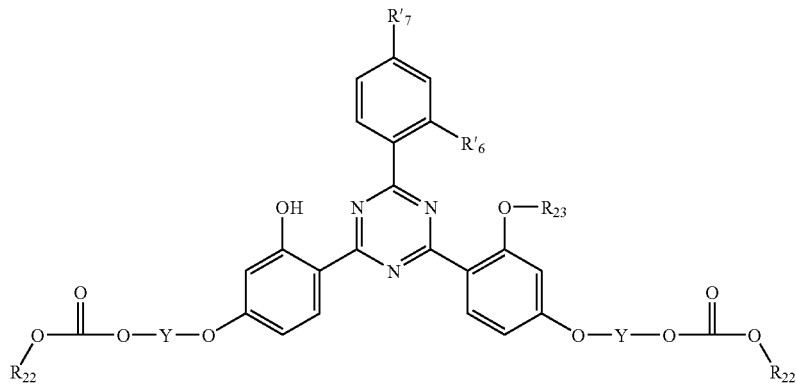

wherein $R'_6$ is H; OH; $C_1$–$C_{12}$alkyl; —O—Y—O—CO—O—$R_{22}$;

$R'_7$ is H; $C_1$–$C_{12}$alkyl; phenyl; $OR'_{10}$;

$R_{10}$ is $C_1$–$C_{12}$alkyl or Y—T;

$R'_{10}$ is $C_1$–$C_{12}$alkyl or Y—O—CO—O—$R_{22}$;

$R_{21}$ is H or Y—T;

$R_{22}$ is phenyl or naphthyl, or phenyl or naphthyl each of which is substituted by $C_1$–$C_8$alkyl;

$R_{23}$ is H or Y—O—CO—O—$R_{22}$;

T is OH or —OCO—CH=$CH_2$ or —OCO—C($CH_3$)=$CH_2$; and

Y is unbranched α,ω-bonded $C_2$–$C_{12}$alkylene or $C_4$–$C_{12}$alkylene interrupted by O; for example the compounds of formulae

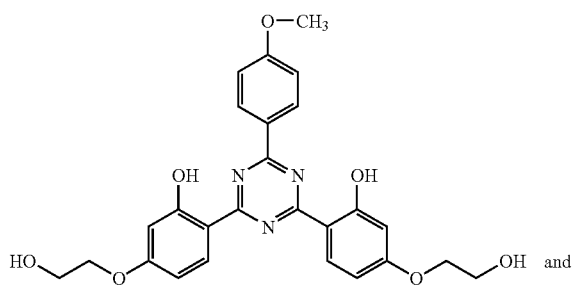and

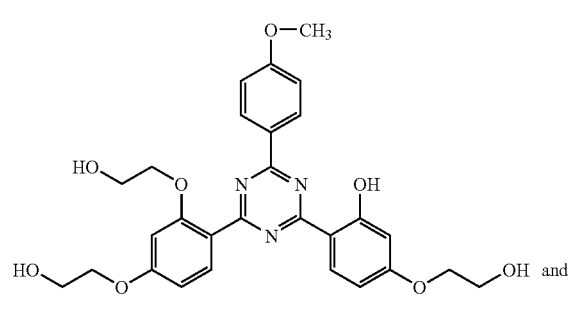and

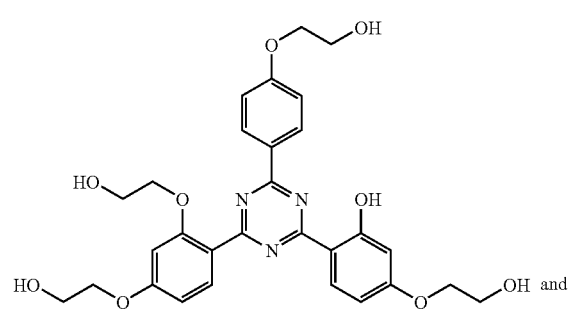and

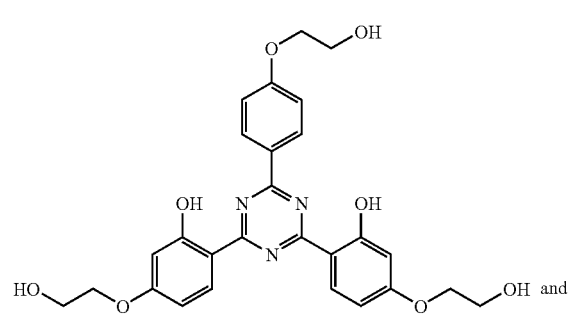and

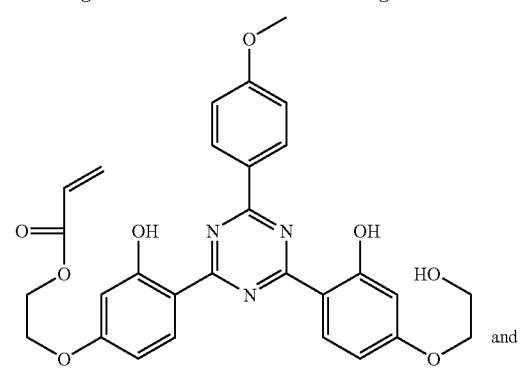and

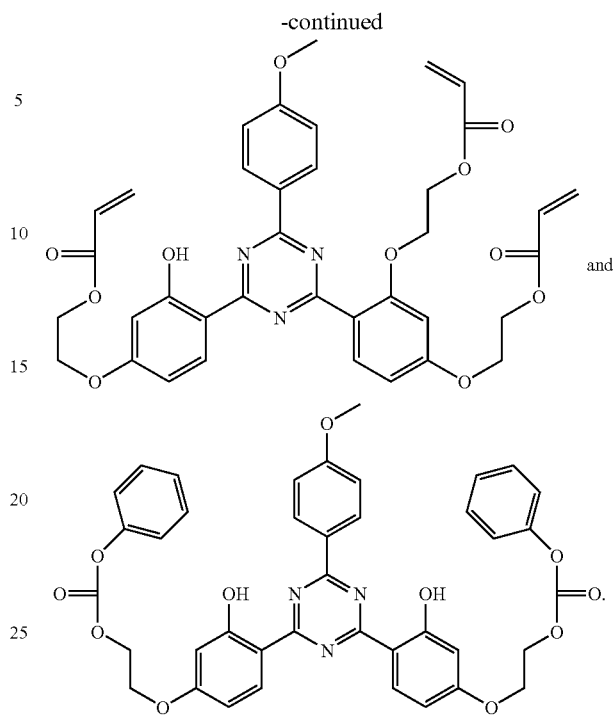

-continued

The polymeric material obtained in the process of present invention effectively reduces the amount of UV light passing through, or even blocks UV light, while preventing migration or blooming of the UV absorbing compound. It may, therefore, be used as an effective UV filter or filter layer.

Content Protection with Reactable UV Absorbers

Thus, a further object of the invention is the protection of foodstuffs, beverages, pharmaceuticals, cosmetics, personal care products, shampoos and the like from the deleterious effects of ultraviolet radiation.

The instant invention therefore includes a method of protecting the content of a clear or lightly colored plastic container or film against the deleterious effects of ultraviolet radiation, which method comprises permanently and covalently bonding one or more UV absorbing moieties of a durable s-triazine UV absorber via condensation to a suitable polymer component.

The instant invention also pertains to clear or lightly colored plastic containers or films for content storage which protect the contents therein against the deleterious effects of ultraviolet radiation and which comprises (a) a polymer component able to undergo a condensation or esterification or transesterification reaction and (b) an effective stabilizing amount of one or more UV absorbing moieties, wherein said moieties are permanently and covalently bonded to the polymer component and are derived, via condensation or esterification or transesterification, from UV absorbers selected from the group consisting of the durable hydroxyphenyl s-triazine UV absorbers.

Suitable polymer components are those able to undergo a condensation or esterification or transesterification reaction;

these are mainly the condensation polymers and their monomeric or oligomeric precursors.

Where the plastic of component (a) is lightly colored it is colored with pigments and/or dyes. Plastic containers and films made therefrom transmit significant portions of radiation of the ultraviolet region, i.e. about 280 to about 400 nm. Ultraviolet absorbers (UVA's) that are red-shifted absorb radiation towards the 400 nm region of the spectrum more efficiently than UVA's that are not red-shifted. Many of the present reactable s-triazines, in addition to being highly durable, are also red-shifted.

The clear or lightly colored plastic of component (a) contains an upper limit of about 5% pigments and/or dyes by weight, in total, based on the weight of the plastic. For instance, the plastic of component (a) contains an upper limit of about 2% by weight pigments and/or dyes based on the weight of the plastic. The upper limit of pigments and/or dyes in the plastic may be for example about 1% by weight.

The UV absorbers of component (b) exhibit excellent compatibility with the plastic containers or films of this invention. Further, they add little or no color to finished plastic containers or films.

The contents to be protected by the compositions and methods of the instant invention include foodstuffs such as fruit juices, soft drinks, beer, wines, food products and dairy products, and personal care products, cosmetics, shampoos, vitamins, pharmaceuticals, inks, dyes and pigments.

The plastic containers and films are rigid or flexible mono- and/or multi-layered packaging materials. The containers and films may comprise polyesters, polyolefins, polyolefin copolymers such as ethylene-vinyl acetate, polystyrene, poly(vinyl chloride), poly(vinylidene chloride), polyamides, cellulosics, polycarbonates, ethylene-vinyl alcohol, poly(vinyl alcohol), styrene-acrylonitrile and ionomers and mixtures or multi-layers of these polymers.

Typical multi-layer constructions have two or more layer laminates, manufactured either by thermoforming, or extrusion of multi-layer flexible films, or extrusion of bottle "preforms" or "parissons" followed by subsequent blow molding of the preforms into bottles.

For both films and rigid packaging (bottles), typically the exterior layer, and innermost layer contacting the contents, are composed of polyesters such as PET or PEN [poly (ethylene naphthalate)], polypropylene, or polyethylene such as HDPE. The middle layers, often-called 'barrier' or 'adhesive' or 'tie' layers, are composed of one or more combinations of either PET, PEN, carboxylated polyethylene ionomer such as Surlyn®, vinyl alcohol homopolymers or copolymers such as poly(vinyl alcohol), partially hydrolyzed poly(vinyl acetate), poly(ethylene-co-vinyl alcohol) such as EVOH or EVAL, nylons or polyamides such as Selar® (DuPont) or polyamides based on metaxylenediamine (sometimes called nylon MXD-6), or polyvinylidene chloride (PVDC), or polyurethanes. For packaging of meats and vegetables, where a controlled rate of 'respiration' or oxygen and moisture transport is desired, polystyrenes and cellulosics are used as a packaging component.

Optionally, the stabilizers of component (b) and optional further additives can be incorporated into coatings which are applied to the outer surface of e.g. rigid containers. Examples of exterior coatings include PVDC, or epoxies (such as Bairocade® technology and polyolefins used as "shrink wrap."

The present containers and films are comprised for example of polyesters, for example poly(ethylene terephthalate) (PET). Where the packaging material is a multi-layer system, layers of any suitable plastic may be employed.

The polyesters which may be used in the compositions of this invention include linear, thermoplastic, crystalline or amorphous polyesters produced by conventional polymerization techniques from one or more diols and one or more dicarboxylic acids. The polyesters normally are molding grade and have an inherent viscosity (I.V.) of about 0.4 to about 1.2. For instance, polyesters comprise at least about 50 mole percent terephthalic acid residues and at least about 50 mole percent ethylene glycol and/or 1,4-cyclohexanedimethanol residues. For example, the present polyesters are those containing from about 75 to 100 mole percent terephthalic acid residues and from about 75 to 100 mole percent ethylene glycol residues.

The diol components of the described polyesters may be selected from ethylene glycol, 1,4-cyclohexanedimethanol, 1,2-propanediol, 1,3-propanediol, 1,4-butanediol, 2,2-dimethyl-1,3-propanediol, 1,6-hexanediol, 1,2-cyclohexanediol, 1,4-cyclohexanediol, 1,2-cyclohexanedimethanol, 1,3-cyclohexanedimethanol, X,8-bis(hydroxymethyl)-tricyclo-[5.2.1.0]-decane wherein X represents 3, 4, or 5; and diols containing one or more oxygen atoms in the chain e.g., diethylene glycol, triethylene glycol, dipropylene glycol, tripropylene glycol and the like. In general, these diols contain 2 to 18, for instance 2 to 8 carbon atoms. Cycloaliphatic diols can be employed in their cis or trans configuration or as mixtures of both forms.

The acid components (aliphatic, alicyclic, or aromatic dicarboxylic acids) of the linear polyester are selected, for example, from terephthalic acid, isophthalic acid, 1,4-cyclohexanedicarboxylic acid, 1,3-cyclohexanedicarboxylic acid, succinic acid, glutaric acid, adipic acid, sebacic acid, 1,12-dodecanedioic acid, 2,6-naphthalene-dicarboxylic acid and the like. In the polymer preparation, functional acid derivative thereof such as the dimethyl, diethyl, or dipropyl ester of the dicarboxylic acid are often employed. The anhydrides or acid halides of these acids also may be employed where practical.

The linear polyesters may be prepared according to procedures well known in the art. For example, a mixture of one or more dicarboxylic acids, for instance aromatic dicarboxylic acids, or ester forming derivatives thereof, and one or more diols may be heated in the presence of esterification and/or poly-esterification catalysts at temperatures in the range of 150° to 300° C. and pressures of atmospheric to 0.2 mm Hg. Normally, the dicarboxylic acid or derivative thereof is esterified or transesterified with the diol(s) at atmospheric pressure and at a temperature at the lower end of the specified range. Polycondensation then is effected by increasing the temperature and lowering the pressure while excess diol is removed from the mixture. Solid state polymerization may be employed to achieve final polymer I.V. in a useful range for films and molded containers.

The novel polyester compositions provided by this invention are useful in the manufacture of containers or packages for comestibles such as beverages and food. By the use of known heat-setting techniques, certain of the polyesters are, in terms of color, I.V. and heat distortion, stable at temperatures up to about 100° C. Such stability characteristics are referred to herein as "hot-fill" stability. Articles molded from these polyesters exhibit good thin-wall rigidity, excellent clarity and good barrier properties with respect to moisture and atmospheric gases, particularly carbon dioxide and oxygen.

Rigid containers may be manufactured by known mechanical processes:
a) Single-stage blow molding such as performed on Nissei, Aoki, or Uniloy machines,
b) Two-stage, injection molding of pre-forms such as on Netstal or Husky machines, and pre-forms converted to bottles by blow molding (e.g., on Sidel, Corpoplast and Krones machines),
c) Integrated blow molding of pre-forms to bottles, such as processes conducted on Sipa, Krupp Kautex, or Husky ISB machines, and
d) Stretch blow molding (SBM) of pre-forms to bottles.

The pre-forms may be mono-layer or multi-layer in construction. The bottles may optionally be post-treated to alter the inner wall properties. Bottles may optionally be surface treated on the exterior such as by application of surface coatings. UV absorbers and other known stabilizers may be present in such added surface coatings.

The linear polyesters for use in articles having "hot-fill" stability comprise for example poly(ethylene terephthalate), poly(ethylene terephthalate) wherein up to 5 mole percent of the ethylene glycol residues have been replaced with residues derived from 1,4-cyclohexanedimethanol and poly(ethylene 2,6-naphthalenedicarboxylate), wherein the polyesters have been sufficiently heat set and oriented by methods well known in the art to give a desired degree of crystallinity. By definition, a polymer is "hot-fill" stable at a prescribed temperature when less than 2% change in volume of a container manufactured therefrom occurs upon filling the same with a liquid at the temperature. For the manufacture of blow-molded beverage bottles, polyesters have for instance an I.V. of 0.65 to 0.85, and a Tg of >70° C., and film sections cut from the bottle have a Water Vapor Transmission Rate of 1.5 to 2.5 g mils/100 in.$^2$ –24 hours, a Carbon Dioxide Permeability of 20 to 30 cc. mils/100 in.$^2$ –24 hours-atm., and an Oxygen Permeability of 4 to 8 cc. mils/100 in.$^2$ –24 hours-atm. The Tg is determined by Differential Scanning Calorimetry at a scan rate of 20 Centigrade Degrees/min., the Oxygen Permeability by the standard operating procedure of a MOCON OXTRAN 100 instrument of Modern Controls, Inc., of Elk Riber, Minn., and the Carbon Dioxide Permeability by the standard operating procedure of a MOCON PERMATRAN C II, also of Modern Controls.

The present hydroxyphenyl s-triazine UV absorbers may be reacted into suitable polymer components of containers and films via condensation reactions. As discussed above, the present containers and films may comprise any of a number of known plastics. However, the reactable s-triazine UV absorbers are necessarily reacted into a polymer component, for example selected from polyesters, polyamides, polycarbonates or copolymers or blends thereof, or reacted together with their monomeric or oligomeric precursors.

The term "reacted into" in this context includes "grafted to", "copolymerized with" and "crosslinked with". The present UV absorbers are permanently and covalently bonded or grafted to the polymer component forming the container or film, mainly by a condensation reaction, which may be an esterification or transesterification, e.g. of a s-triazine UV absorber containing a reactable hydroxy or ester or carbonate group and a corresponding polymer or precursor thereof as described above.

The present hydroxyphenylbenzotriazole and s-triazine UV absorbers may be reacted into a component of a container or film during a polymerization process or may be reacted with a partially formed polymer or may be reacted with a finished polymer. The present UV absorbers may be reacted with monomers prior to their polymerization into a polymer component, or may be reacted with a partially formed polymer at any point during a polymerization process. If reacted with a finished polymer, the present UV absorbers are grafted onto the polymer via reaction with the polymer's end groups.

The hydroxyphenyl s-triazine UV absorbers may be grafted into a polymer at a high level, thereby providing a masterbatch of UV absorbing polymer component. Such a masterbatch may further be let down with a conventional polymer. A masterbatch may contain component (b) in a concentration of, for example, about 2.5% to about 95% by weight based on the weight of the polymer component (a). For example, a masterbatch of this invention may contain component (b) in a concentration of, for example, about 5% to about 80%, or about 10% to about 70%, or about 20% to about 50%, or about 25% to about 35%.

The polymer reacted, or grafted with the present reactable, durable UV absorbers, for example the masterbatches described above, are considered UV absorbing polymers.

The condensation-reactable hydroxyphenyl s-triazine UV absorbers described herein are in their "pre-reaction" form, that is in the form to be reacted with the appropriate polymer. Once reacted with the polymer component, the present UV absorbers are part of a "UV absorbing polymer" as "UV absorbing moieties". Said moieties are equivalent to the pre-reaction UV absorber in structure less the chemical group discharged in the condensation reaction, for example less a hydrogen, hydroxy or alkoxy. Alternatively, the UV moiety may gain a chemical group, for example, a hydrogen may be gained if a reaction between a hydroxy of a polymer and an epoxy of a UV absorber takes place. The bonded moieties are derived from the reactable UV absorbers disclosed herein.

The reactable groups of the present hydroxyphenylbenzotriazole and s-triazine UV absorbers of component (b) are typical groups they may under condensation reactions, for example carboxylic acids, esters, alcohols, epoxides, glycidyl groups, amides and amines. The hydroxyphenylbenzotriazole and s-triazine UV absorbers may contain a single reactive group, and hence would function as a chain termination agent. Alternatively, they may have 2 or more reactive groups, and then have the ability to copolymerize into the reactable polymer.

Suitable catalysts may be employed for the present UV absorber-polymer condensation reactions. For example, suitable esterification catalysts.

The reactable, durable tris-aryl-s-triazines of the instant invention are typical commercial s-triazine UV absorbers based on 4,6-bis-(2,4-dimethylphenyl)-2-(2,4-dihydroxyphenyl)-s-triazine such as Tinuvin® 400, Ciba Specialty Chemicals Corp., or they are based on red-shifted s-triazines as disclosed for example in U.S. Pat. Nos. 5,556,973 and 5,354,794, or they are based on high molar extinction s-triazines as disclosed in U.S. Pat. No. 6,255,483.

The s-triazine UV absorbers of component (b) are of formula (IV), (V), (VI), (VII), (VIII) or (IX)

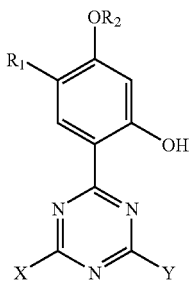
(IV)

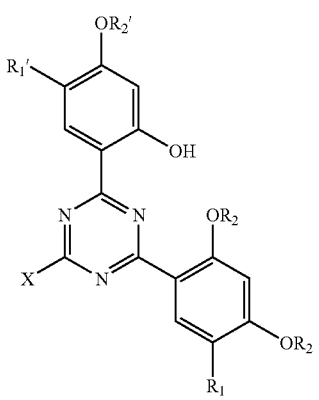
(V)

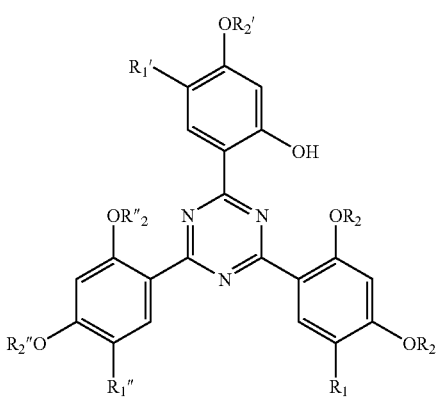
(VI)

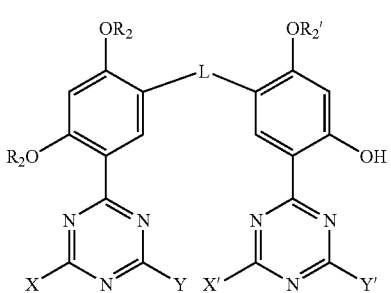
(VII)

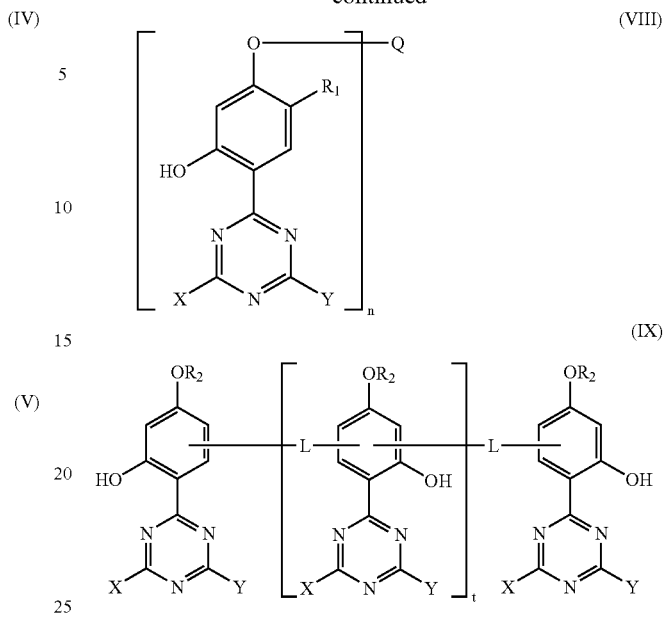

wherein

X and Y are independently phenyl, naphthyl, or said phenyl or said naphthyl substituted by one to three alkyl of 1 to 6 carbon atoms, by halogen, by hydroxy or by alkoxy of 1 to 6 carbon atoms or by mixtures thereof; or X and Y are independently $Z_1$ or $Z_2$;

$R_1$ is hydrogen, straight or branched chain alkyl of 1 to 24 carbon atoms, cycloalkyl of 5 to 12 carbon atoms, phenylalkyl of 7 to 15 carbon atoms, halogen, —$SR_3$, —$SOR_3$ or —$SO_2R_3$; or said alkyl, said cycloalkyl or said phenylalkyl substituted by one to three halogen, —$R_4$, —$OR_5$, —$N(R_5)_2$, —$COR_5$, —$COOR_5$, —$OCOR_5$, —CN, —$NO_2$, —$SR_5$, —$SOR_5$, —$SO_2R_5$ or —$P(O)(OR_5)_2$, morpholinyl, piperidinyl, 2,2,6,6-tetramethylpiperidinyl, piperazinyl or N-methylpiperidinyl groups or combinations thereof; or said alkyl or said cycloalkyl interrupted by one to four phenylene, —O—, —$NR_5$—, —$CONR_5$—, —COO—, —OCO— or —CO groups or combinations thereof; or said alkyl or said cycloalkyl both substituted and interrupted by combinations of the groups mentioned above;

$R_3$ is alkyl of 1 to 20 carbon atoms, alkenyl of 3 to 18 carbon atoms, cycloalkyl of 5 to 12 carbon atoms, phenylalkyl of 7 to 15 carbon atoms, aryl of 6 to 10 carbon atoms or said aryl substituted by one or two alkyl of 1 to 4 carbon atoms;

$R_4$ is aryl of 6 to 10 carbon atoms or said aryl substituted by one to three halogen, alkyl of 1 to 8 carbon atoms, alkoxy of 1 to 8 carbon atoms or combinations thereof; cycloalkyl of 5 to 12 carbon atoms; phenylalkyl of 7 to 15 carbon atoms or said phenylalkyl substituted on the phenyl ring by one to three halogen, alkyl of 1 to 8 carbon atoms, alkoxy of 1 to 8 carbon atoms or combinations thereof; or straight or branched chain alkenyl of 2 to 18 carbon atoms;

$R_5$ is defined as is $R_4$; or $R_5$ is also hydrogen or straight or branched chain alkyl of 1 to 24 carbon atoms, alkenyl of 2 to 24 carbon atoms; or $R_5$ is a group for formula

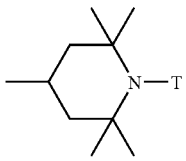

T is hydrogen, oxyl, hydroxyl, —OT$_1$, alkyl of 1 to 24 carbon atoms, said alkyl substituted by one to three hydroxy; benzyl or alkanoyl of 2 to 18 carbon atoms;

T$_1$ is alkyl of 1 to 24 carbon atoms, cycloalkyl of 5 to 12 carbon atoms, alkenyl of 2 to 24 carbon atoms, cycloalkenyl of 5 to 12 carbon atoms, phenylalkyl of 7 to 15 carbon atoms, a radical of a saturated or unsaturated bicyclic or tricyclic hydrocarbon of 7 to 12 carbon atoms or aryl of 6 o 10 carbon atoms or said aryl substituted by one to three alkyl of 1 to 4 carbon atoms;

R$_2$ is hydrogen, straight or branched chain alkyl of 1 to 24 carbon atoms or cycloalkyl of 5 to 12 carbon atoms; or said alkyl or said cycloalkyl substitute by one to four halogen, epoxy, glycidyloxy, furyloxy, —R$_4$, —OR$_5$, —N(R$_5$)$_2$, —CON(R$_5$)$_2$, —COR$_5$, —COOR$_5$, —OCOR$_5$, —OCOC(R$_5$)=C(R$_5$)$_2$, —C(R$_5$)=CCOOR$_5$, —CN, —NCO, or

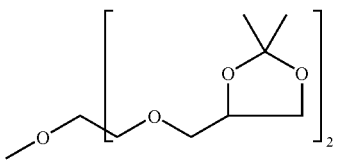

or combinations thereof; or said alkyl or said cycloalkyl interrupted by one to four epoxy, —O—, —NR$_5$—, —CONR$_5$—, —COO—, —OCO—, —CO—, —C(R$_5$)=C(R$_5$)COO—, —OCOC(R$_5$)=C(R$_5$)—, —C(R$_5$)=C(R$_5$)—, phenylene or phenylene-G-phenylene in which G is —O—, —S—, —SO$_2$—, —CH$_2$— or —C(CH$_3$)$_2$— or combinations thereof, or said alkyl or said cycloalkyl both substituted and interrupted by combinations of the groups mentioned above; or R$_2$ is —SO$_2$R$_3$ or —COR$_6$;

R$_6$ is straight or branched chain alkyl of 1 to 18 carbon atoms, straight or branched chain alkenyl of 2 to 12 carbon atoms, phenoxy, alkylamino of 1 to 12 carbon atoms, arylamino of 6 to 12 carbon atoms, —R$_7$COOH or —NH—R$_8$—NCO;

R$_7$ is alkylene of 2 to 14 carbon atoms or phenylene;

R$_8$ is alkylene of 2 to 24 carbon atoms, phenylene, tolylene, diphenyl-methane or a group

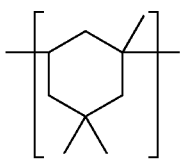

R$_1$' and R$_1$" are the same or different and are as defined for R$_1$;

R$_2$' and R$_2$" are the same or different and are as defined for R$_2$;

X, X', Y and Y' are the same or different and are as defined for X and Y;

t is 0 to 9;

L is straight or branched alkylene of 1 to 12 carbon atoms, cycloalkylene of 5 to 12 carbon atoms or alkylene substituted or interrupted by cyclohexylene or phenylene; or L is benzylidene; or L is —S—, —S—S—, —S-E-S—, —SO—, —SO$_2$—, —SO-E-SO—, —SO$_2$-E-SO$_2$—, —CH$_2$—NH-E-NH—CH$_2$— or

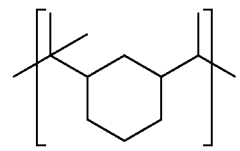

E is alkylene of 2 to 12 carbon atoms, cycloalkylene of 5 to 12 carbon atoms or alkylene interrupted or terminated by cycloalkylene of 5 to 12 carbon atoms;

n is 2, 3 or 4;

when n is 2; Q is straight or branched alkylene of 2 to 16 carbon atoms; or said alkylene substituted by one to three hydroxy groups; or said alkylene interrupted by one to three —CH=CH— or —O—; or said alkylene both substituted and interrupted by combinations of the groups mentioned above; or Q is xylylene or a group —CONH—R$_8$—NHCO—, —CH$_2$CH(OH)CH$_2$O—R$_9$—OCH$_2$CH(OH)CH$_2$—, —CO—R$_{10}$—CO—, or —(CH$_2$)$_m$—COO—R$_{11}$—OOC—(CH$_2$)$_m$—, where m is 1 to 3; or Q is

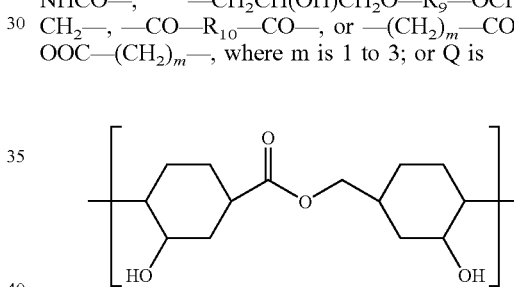

R$_9$ is alkylene of 2 to 50 carbon atoms; or said alkylene interrupted by one to ten —O—, phenylene or a group -phenylene-G-phenylene in which G is —O—, —S—, —SO$_2$—, —CH$_2$— or —C(CH$_3$)$_2$—;

R$_{10}$ is alkylene of 2 to 10 carbon atoms, or said alkylene interrupted by one to four —O—, —S— or —CH=CH—; or R$_{10}$ is arylene of 6 to 12 carbon atoms;

R$_{11}$ is alkylene of 2 to 20 carbon atoms or said alkylene interrupted by one to eight —O—;

when n is 3, Q is a group —[(CH$_2$)$_m$COO]$_3$—R$_{12}$ where m is 1 to 3, and R$_{12}$ is an alkanetriyl of 3 to 12 carbon atoms;

when n is 4, Q is a group —[(CH$_2$)$_m$COO]$_4$—R$_{13}$ where m is 1 to 3, and R$_{14}$ is an alkanetetrayl of 4 to 12 carbon atoms;

Z$_1$ is a group of formula

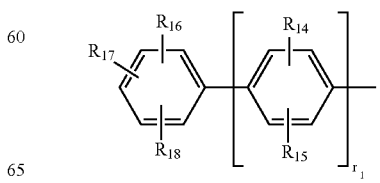

$Z_2$ is a group of formula

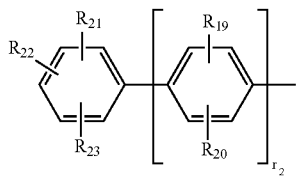

where
$r_1$ and $r_2$ are independently of each other 0 or 1;
$R_{14}$, $R_{15}$, $R_{16}$, $R_{17}$, $R_{18}$, $R_{19}$, $R_{20}$, $R_{21}$, $R_{22}$ and $R_{23}$ are independently of one another hydrogen, hydroxy, cyano, alkyl of 1 to 20 carbon atoms, alkoxy of 1 to 20 carbon atoms, phenylalkyl of 7 to 15 carbon atoms, cycloalkyl of 5 to 12 carbon atoms, cycloalkoxy of 5 to 12 carbon atoms, halogen, haloalkyl of 1 to 5 carbon atoms, sulfo, carboxy, acylamino of 2 to 12 carbon atoms, acyloxy of 2 to 12 carbon atoms, alkoxycarbonyl of 2 to 12 carbon atoms or aminocarbonyl; or $R_{17}$ and $R_{18}$ or $R_{22}$ and $R_{23}$ together with the phenyl radical to which they are attached are a cyclic radical interrupted by one to three —O— or —$NR_5$—;

with the proviso that at least one of X, X', Y, Y' is substituted by at least one hydroxy that is not ortho to the s-triazine ring, or at least one of —$OR_2$, —$OR_2$' and —$OR_2$" in a para position to the s-triazine ring is —OH, or at least one of $R_1$, $R_1$', $R_1$", $R_2$, $R_2$' and $R_2$" is alkyl, cycloalkyl or phenylalkyl substituted by at least one —OH, —$COOR_5$, —$NHR_5$, —$CONHR_5$, —NCO, epoxy or glycidyloxy.

For instance, the invention pertains to compounds of formula (IV) where X and Y are the same or different and are phenyl or said phenyl substituted by one to three alkyl of 1 to 6 carbon atoms, halogen, hydroxy or alkoxy of 1 to 12 carbon atoms; or X and Y are $Z_1$ or $Z_2$;

$R_1$ is hydrogen, straight or branched chain alkyl of 1 to 24 carbon atoms, cycloalkyl of 5 to 12 carbon atoms, phenylalkyl of 7 to 15 carbon atoms or halogen;

$R_2$ is hydrogen, straight or branched chain alkyl of 1 to 24 carbon atoms or cycloalkyl of 5 to 12 carbon atoms; or said alkyl or said cycloalkyl substituted by one to three —$R_4$, —$OR_5$, —$COOR_5$, —$OCOR_5$ or combinations thereof; or said alkyl or cycloalkyl interrupted by one to three epoxy, —O—, —COO—, —OCO— or —CO—;

$R_4$ is aryl of 6 to 10 carbon atoms or said aryl substituted by one to three halogen, alkyl of 1 to 8 carbon atoms, alkoxy of 1 to 8 carbon atoms or combinations thereof; cycloalkyl of 5 to 12 carbon atoms; phenylalkyl of 7 to 15 carbon atoms or said phenylalkyl substituted on the phenyl ring by one to three halogen, alkyl of 1 to 8 carbon atoms, alkoxy of 1 to 8 carbon atoms or combinations thereof;

$R_5$ is defined as is $R_4$; or $R_5$ is also hydrogen or straight or branched chain alkyl of 1 to 24 carbon atoms;

$Z_1$ is a group of formula

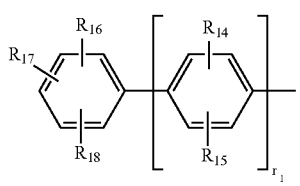

$Z_2$ is a group of formula

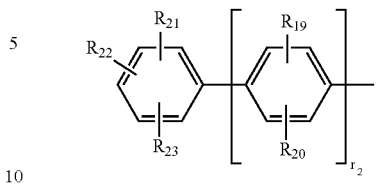

where $r_1$ and $r_2$ are each 1; and
$R_{14}$, $R_{15}$, $R_{16}$, $R_{17}$, $R_{18}$, $R_{19}$, $R_{20}$, $R_{21}$, $R_{22}$ and $R_{23}$ are independently of one another hydrogen, hydroxy, cyano, alkyl of 1 to 20 carbon atoms, alkoxy of 1 to 20 carbon atoms, phenylalkyl of 7 to 15 carbon atoms, cycloalkyl of 5 to 12 carbon atoms, cycloalkoxy of 5 to 12 carbon atoms, halogen, haloalkyl of 1 to 5 carbon atoms, sulfo, carboxy, acylamino of 2 to 12 carbon atoms, acyloxy of 2 to 12 carbon atoms, or alkoxycarbonyl of 2 to 12 carbon atoms or aminocarbonyl;

with the proviso that at least one of X and Y is substituted by at least one hydroxy that is not ortho to the s-triazine ring, or —$OR_2$ is —OH, or $R_2$ is alkyl or cycloalkyl substituted by at least one —OH or —$COOR_5$.

For example, the s-triazine UV absorber is also of formula (V) where

X is phenyl, naphthyl or said phenyl or said naphthyl substituted by one to three alkyl of 1 to 6 carbon atoms, by halogen, by hydroxy or by alkoxy of 1 to 6 carbon atoms or by mixtures thereof; or X is $Z_1$, with the proviso that X is substituted by at least one hydroxy that is not ortho to the s-triazine ring, or that the s-triazine otherwise contains a condensation reactable group as described above.

For example, the s-triazine UV absorber is also of formula (VI), (VII) or (VIII) that contains a condensation reactable group as above.

For instance, the s-triazine UV absorber is also of formula (IX) where

X and Y are independently phenyl or said phenyl substituted by one to three alkyl of 1 to 6 carbon atoms, by halogen, by hydroxy or by alkoxy of 1 to 6 carbon atoms or by mixtures thereof; or X and Y are independently $Z_1$ or $Z_2$; and L is straight or branched alkylene of 1 to 12 carbon atoms, cycloalkylene of 5 to 12 carbon atoms or alkylene substituted or interrupted by cyclohexylene or phenylene;

with the provisio that the s-triazine contains a condensation reactable group as described above.

For instance, the instant s-triazine UV absorber is of formula (IV) where X and Y are the same or different and are phenyl or said phenyl substituted by one to three alkyl of 1 to 6 carbon atoms; $Z_1$ or $Z_2$;

$R_1$ is hydrogen or phenylalkyl of 7 to 15 carbon atoms;

$R_2$ is hydrogen, straight or branched chain alkyl of 1 to 18 carbon atoms; or said alkyl substituted by one to three —$R_4$, —$OR_5$ or mixtures thereof; or said alkyl interrupted by one to eight —O— or —COO—;

$R_4$ is aryl of 6 to 10 carbon atoms;
$R_5$ is hydrogen;
$Z_1$ is a group of formula
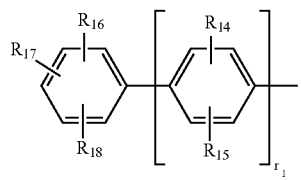
$Z_2$ is a group of formula
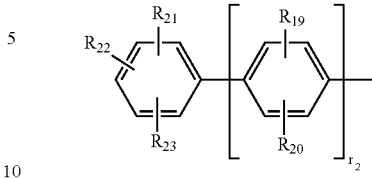
where
$r_1$ and $r_2$ are each 1; and
$R_{14}$, $R_{15}$, $R_{16}$, $R_{17}$, $R_{18}$, $R_{19}$, $R_{20}$, $R_{21}$, $R_{22}$ and $R_{23}$ are each hydrogen;
with the proviso that the s-triazine contains a condensation reactable group.
For example, the s-triazine UV absorber of this invention is a compound which is
(c1)
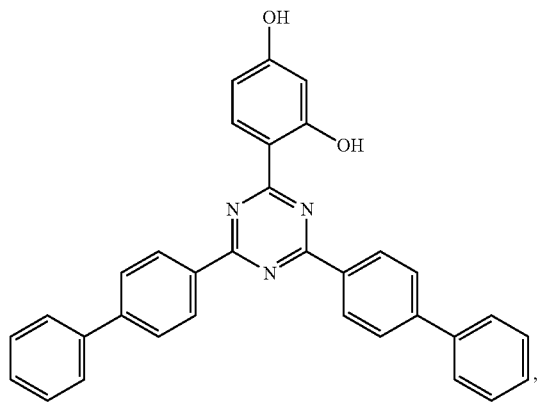
(c2)
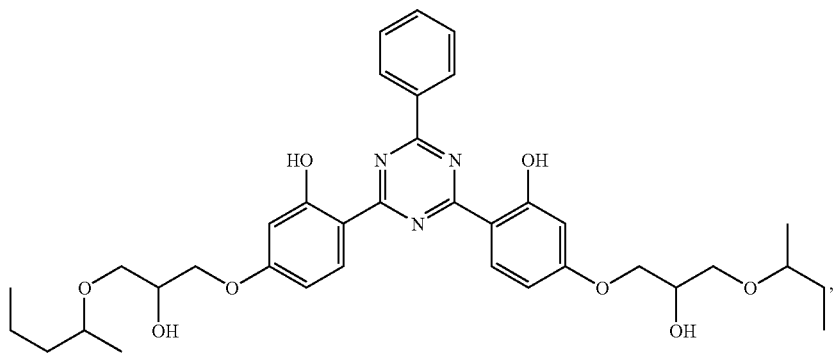

-continued
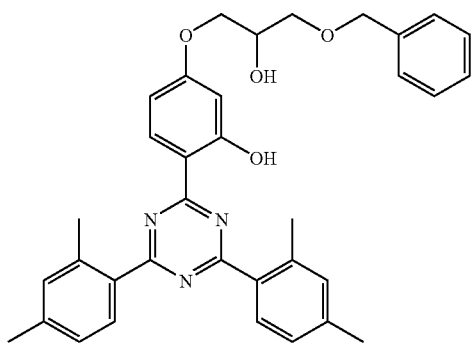 (c3)
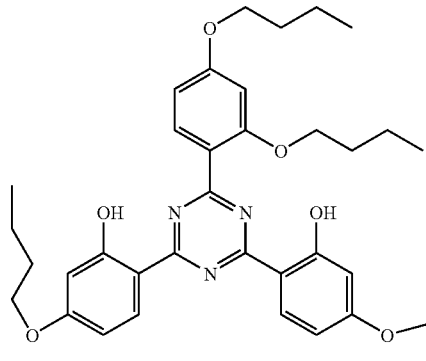 (c4)
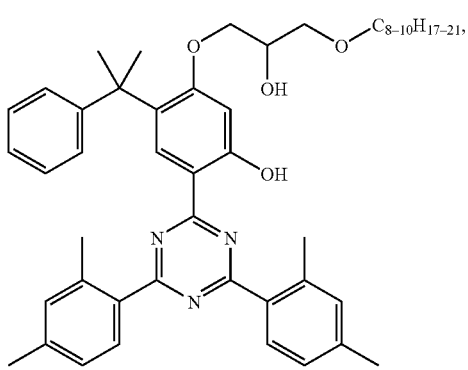 (c5)
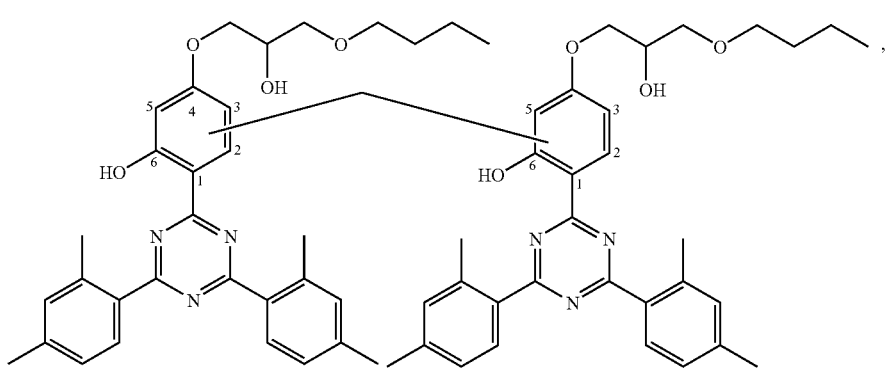 (c6)

methylene bridged dimer mixture bridged in the 3:5', 5:5' and 3:3' positions in a 5:4:1 ratio
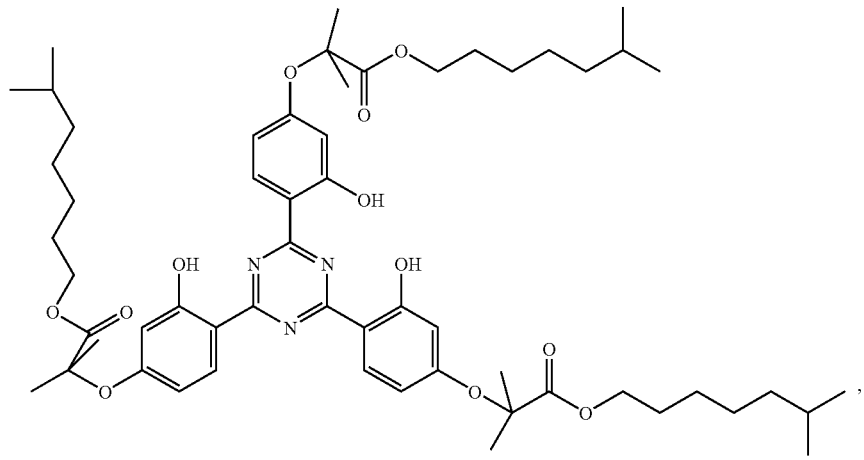
(c7)
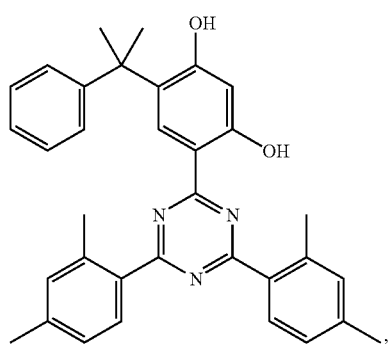
(c8)
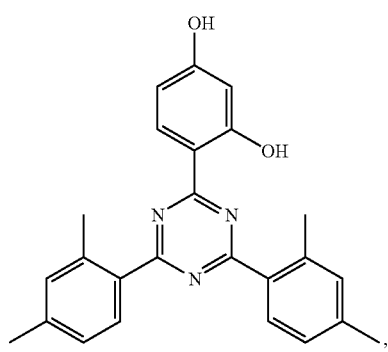
(c9)
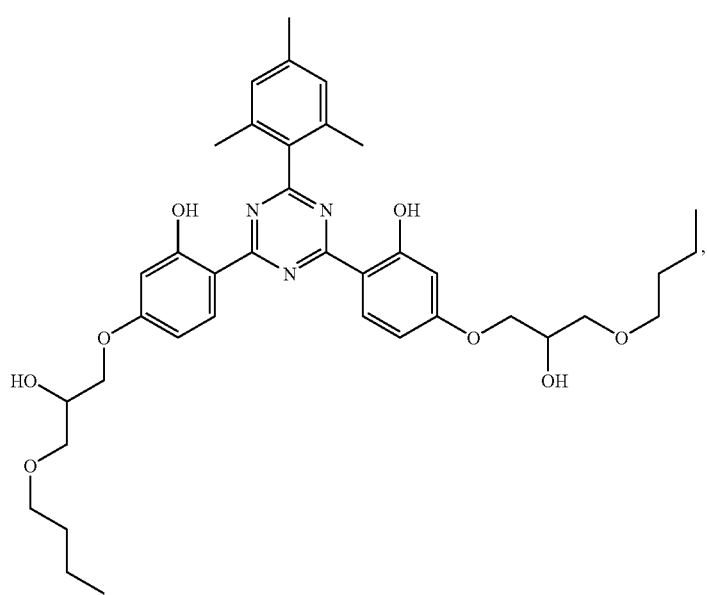
(c10)

-continued

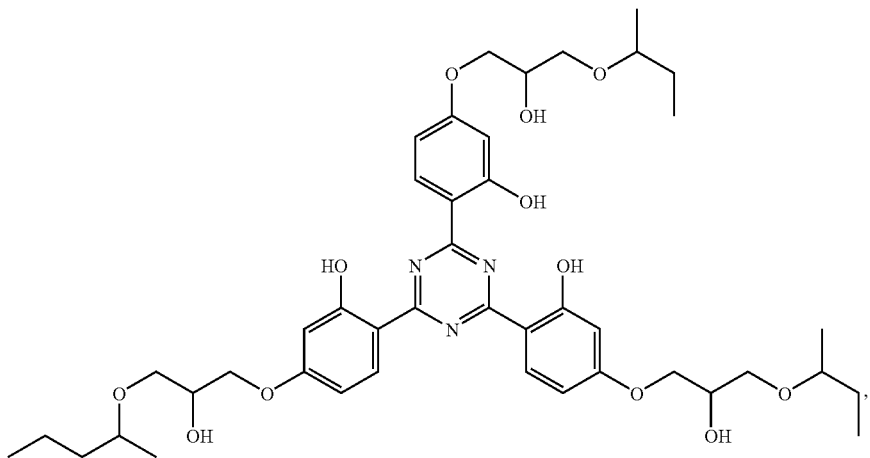

(c11)

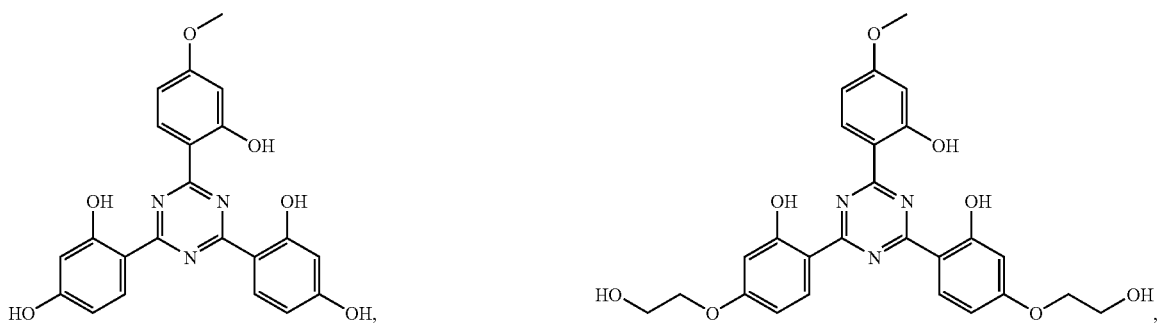

(c12) (c13)

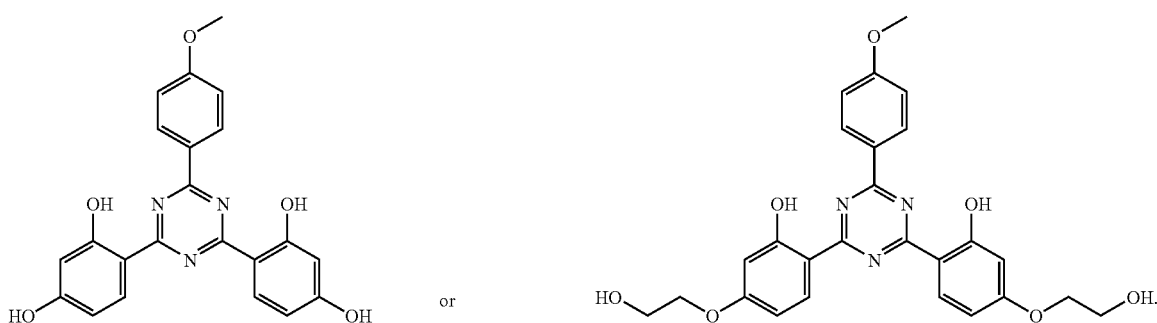

(c14) or (c15)

The effective stabilizing amount of the compound or compounds of component (b) is about 0.01 to about 20% by weight based on the weight of the plastic container or film composition, for example 0.05 to about 10%, depending mainly on thickness and type of the polymer material or container or film and the intensity of UV radiation.

According to the present invention, the compositions may also comprise another UV absorber not of the reactable class described herein. Suitable additional UV absorbers are for example durable benzotriazole and triazines as disclosed in copending U.S. application Ser. No. 09/772,245, filed Jan. 29, 2001, the disclosure of which is hereby incorporated by reference. The present compositions may comprise additional commercial benzotriazole and/or s-triazine UV absorbers as described herein. For example a suitable additional UV absorber may be selected from 2-(2-hydroxy-3,5-di-α-cumyl)-2H-benzotriazole, 5-chloro-2-(2-hydroxy-3-tert-butyl-5-methylphenyl)-2H-benzotriazole, 5-chloro-2-(2-hydroxy-3,5-di-tert-butylphenyl)-2H-benzotriazole and 4,6-diphenyl-2-(4-hexyloxy-2-hydroxyphenyl)-s-triazine.

The instant plastic container or film stabilized by a compound or compounds of component (b) may also optionally contain from about 0.01 to about 10% by weight; for instance from about 0.025 to about 5% by weight, for example from about 0.1 to about 3% by weight of additional coadditives such as antioxidants, other UV absorbers, hindered amines, phosphites or phosphonites, hydroxylamines, nitrones, benzofuran-2-ones, thiosynergists, polyamide stabilizers, metal stearates, nucleating agents, fillers, reinforcing agents, lubricants, emulsifiers, dyes, pigments, optical brighteners, flame retardants, antistatic agents, blowing agents and the like (see list further above), or mixtures thereof.

The stabilizers of the instant invention may readily be incorporated into the present container or film compositions by conventional techniques, at any convenient stage prior to the manufacture of articles therefrom. For example, the stabilizer may be mixed with the polymer in dry powder form, or a suspension or emulsion of the stabilizer may be mixed with a solution, suspension, or emulsion of the polymer.

The examples which follow illustrate the invention further. All parts or percentages, both in the examples and in the remainder of the description and in the patent claims, are by weight, unless stated otherwise. Abbreviations used:

m.p. melting point or range (in ° C. if not otherwise indicated);

PET poly ethylene terephthalate

OH-functional Compounds of Formula I' Used:

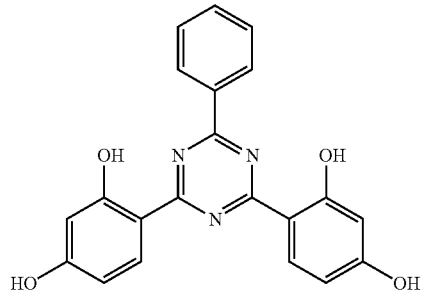

1.

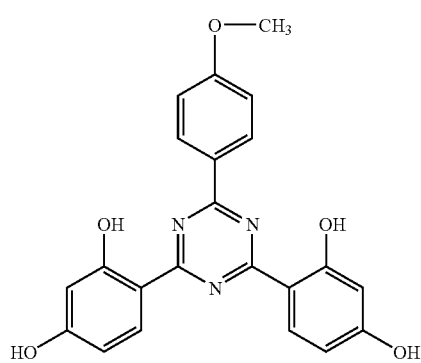

2.

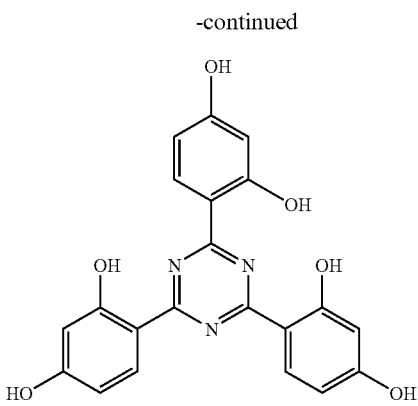

3.

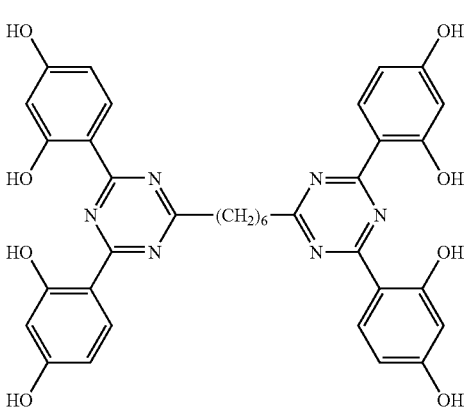

4.

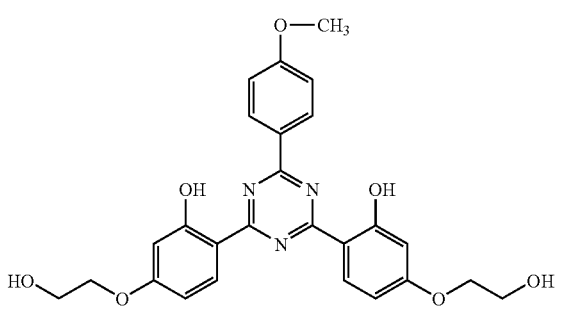

5.

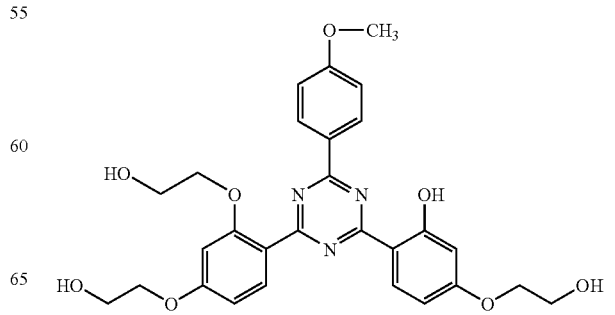

6.

-continued

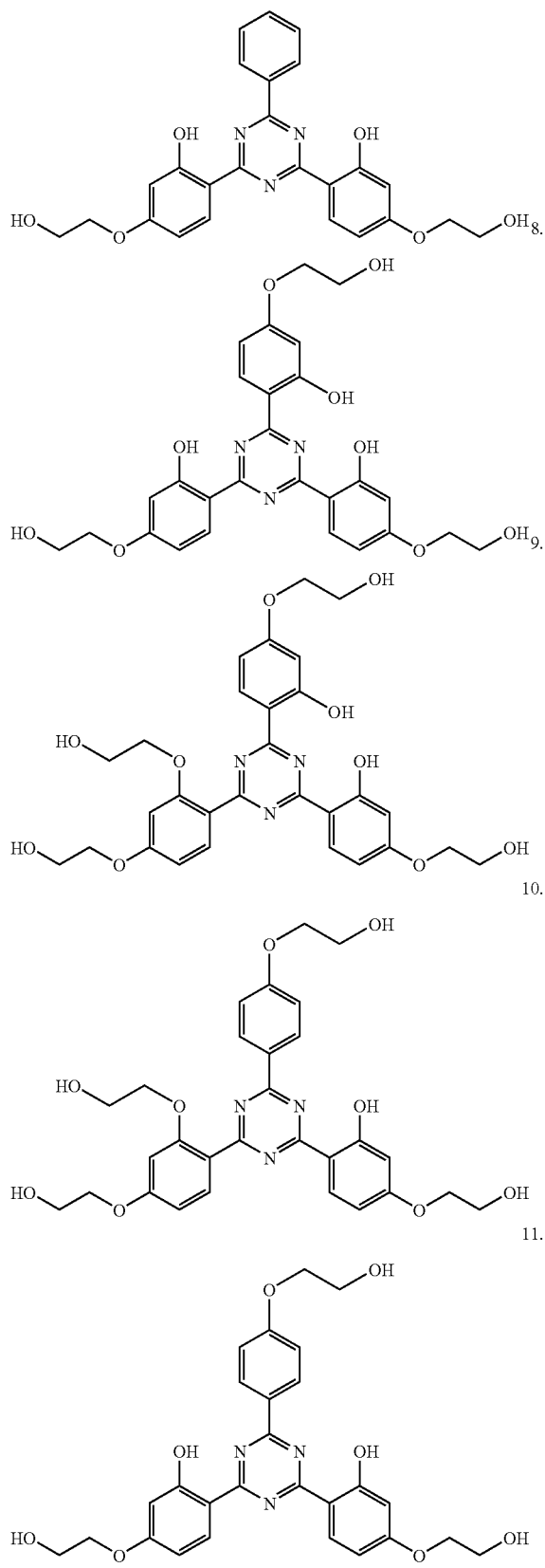

7.
8.
9.
10.
11.

Further compounds usable as crosslinkers are described in the below examples.

A: PREPARATION EXAMPLES

Example A1

Synthesis of the compound No. 5 of formula:

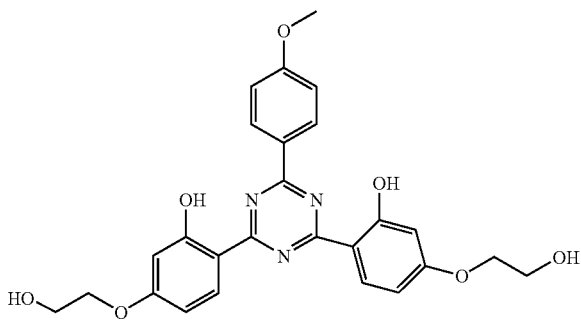

A suspension of 20 g (0.05 mole) of 2-(4-methoxyphenyl)-4,6-bis(2,4-dihydroxyphenyl)-1,3,5-triazine in 100 ml ethylcellosolve is heated to 70° C. 44 g potassium carbonate are added and 40.16 g (0.32 mole) 2-bromoethanol are added dropwise over 2 hrs. The mixture is heated for a further 3 hours at 70° C., then filtered hot to remove inorganic salts. The filtrate is cooled to 0° C. and allowed to crystallise. The solid is filtered off and dried at 60° C. under vacuum, yielding 11.1 g of 2-(4-methoxylphenyl)-4,6-bis(2-hydroxy-4-(2-ethoxyethoxy)phenyl)-1,3,5-triazine as a yellow powder, m.p. 155–158° C.

Example A2

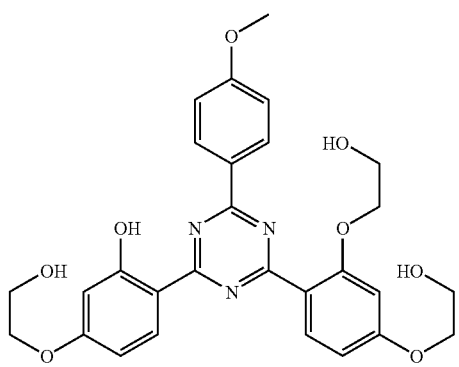

2-(4-methoxyphenyl)-4-[2-hydroxy-4-(2-hydroxyethoxy)-phenyl]-6-[2,4-bis-(2-hydroxyethoxy)-phenyl]-1,3,5 triazine 2-(4-Methoxyphenyl)-4,6-bis(2,4-dihydroxyphenyl)-1,3,5-triazine (50 g) is suspended in 200 ml DMF and heated to 90° C. Benzyltriphenylphosphonium chloride (0.56 g), is added followed by addition of ethylenecarbonate (36.0 g). The resulting mixture is heated at 135° C. for 10 hours. The solvent is removed by evaporation under reduced pressure and the residual oil dissolved in 100 ml hot methanol. The solution is cooled to 0° C. and the crystals filtered off, washed with 100 ml cold methanol and 100 ml water. The pale yellow solid is dried under reduced pressure to give 2-(4 methoxyphenyl)-4-[2-hydroxy-4-(2-hydroxyethoxy)-phenyl]-6-[2,4-bis-(2-hydroxyethoxy)-phenyl]-1,3,5.triazine (31.5 g) with mp. 172° C.

Example A3

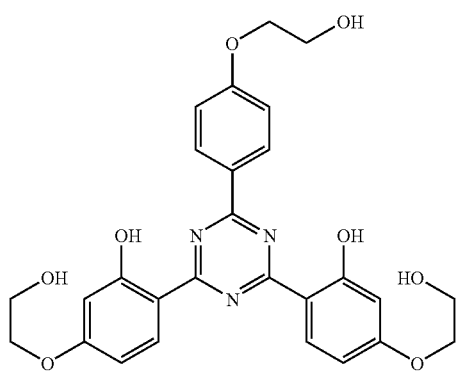

2-[4-(2-hydroxyethoxy)phenyl]-4,6-bis-[2-hydroxy-4-(2-hydroxyethoxy) phenyl]-1,3,5-triazine (compound No. 11)

2-[4-Hydroxyphenyl)-4,6-bis-(2,4-dihydroxyphenyl)-1,3,5-triazine (10 g) is suspended in 100 ml 2 ethoxyethanol and heated to 100° C. Benzyltriphenylphosphonium chloride (0.12 g) is added followed by ethylenecarbonate (8.59 g) over a period of 7 hours. The reaction mixture is stirred at 135° C. for 10 hours then cooled to RT. The crystals are filtered off, washed with 100 ml cold methanol and 100 ml cold water and dried under reduced pressure. The title compound (9.0 g) is obtained with mp 169° C.

Example A4

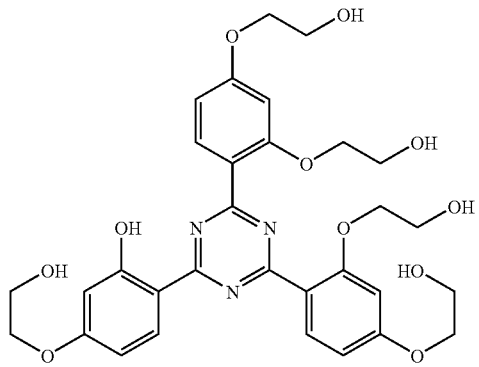

2-[2-hydroxy-4-(2 hydroxyethoxy)phenyl]-4,6-bis-[2,4-bis-(2-hydroxyethoxy)phenyl]-1,3,5-triazine 2,4,6-Tris-(2,4-dihydroxyphenyl)-1,3,5-triazine (20.0 g) is suspended on 100 ml DMF and heated to 75° C. Benzyltriphenylphosphonium bromide (0.14 g) is added, followed by ethylenecarbonate (26.05 g). The mixture is heated at 135° C. for 5 hours, cooled and concentrated under reduced pressure. The residue is chromatogrphed over SiO₂ using ethylacetate/methanol 8:2 as eluant. The title compound (26.0 g) is obtained as light orange oil.

Example A5

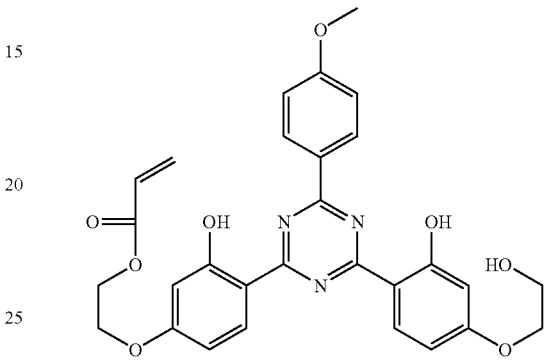

2-(4-Methoxyphenyl)-4-[2-hydroxy-4-(2-hydroxyethoxy)phenyl]-6-[2-hydroxy-4-(2-acroyloxyethoxy)-phenyl]-1,3,5-triazine 2-(4-Methoxyphenyl)-4,6-bis[2-hydroxy-4-(2-hydroxyethoxy) phenyl]-1,3,5-triazine (10 g) is suspended in 100 ml THF and cooled to 0° C. Triethylamine (2.06 g) and acroylchloride (1.84 g) are added and the mixture stirred for 3 hours at room temperature. The same quantities of triethylamine and acroylchloride are added and the mixture stirred for a further 3 hours. After removing the salts formed by filtration the mother liquor is evaporated under reduced pressure. The residue is chromatographed over SiO₂ using toluene/ethylacetate 1:1 as eluant. The title compound (2.0 g) is obtained as a pale yellow solid mp 109° C.

Example A6

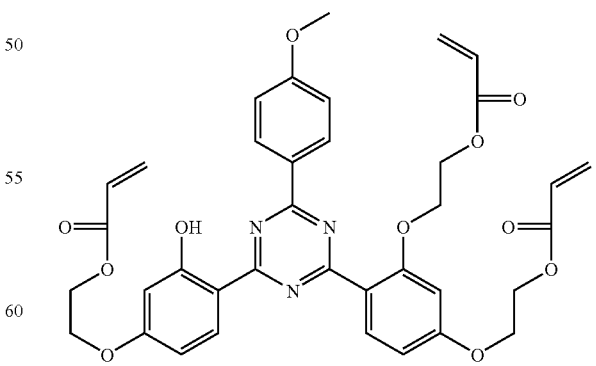

2-(4-Methoxyphenyl)-4-[(2-hydroxy-4-(2-acroyloxyethoxy) phenyl]-6-[2,4-bis-(2-acroyloxy(ethox)yphenyl]-1,3,5-triazine 2-(4-Methoxyphenyl)-4-[2-hydroxy-4 (2-hydroxyethoxyphenyl]-6-[2,4-bis-(2-hydrxyethoxyphenyl)]-1,3,5-triazine (10.0 g) is suspended in 100 ml THF and cooled to 5° C. Triethylamine (9.45 g) followed by acroylchloride (8.45 g) are added keeping the temperature below 10° C. The reaction mixture is then stirred 16 hours at room temperature before removing the salts by filtration. The solvent is removed under reduced pressure and the residue chromatographed over SiO₂ using toluene/ethylacetate 3:1 as eluant. The title compound (4.2 g) is obtained as a yellow oil.

Example A7

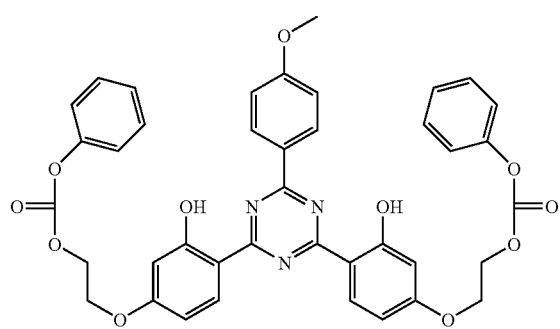

2-(4-Methoxylphenyl)-4,6-bis-2-hydroxyl-4-[2-(phenoxy-carboxyloxy) ethoxy]-phenyl-1,3,5-triazine 2-(4 Methoxylphenyl)-4,6-bis[2-hydroxy-4-(2-hydroxyethoxy)phenyl]-1,3,5-triazine (20.0 g) and diphenylcarbonate (87.1 g) are heated together to 200° C. and held there for 3 hours. The reaction mass is cooled to room temperature and suspended in 100 ml hot ethanol. The ethanol suspended is cooled to 5° C. and got filtered. The solid is washed with 100 ml cold ethanol and 100 ml water then dried under reduced pressure. The title compound (16.1 g) is obtained as pale yellow crystals mp. 130° C.

Example A8

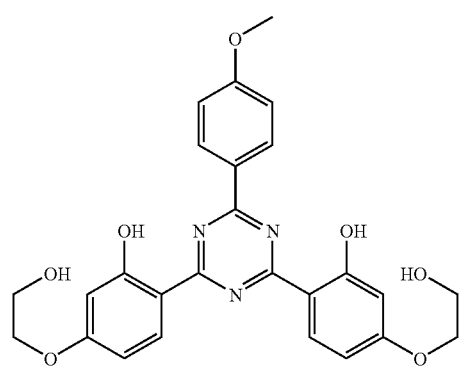

2-(4-Methoxyphenyl)-4,6-bis-[2-hydroxy-4-(2-hydroxyethoxy)-phenyl]-1,3,5-triazine 2-(4-Methoxyphenyl)-4,6-bis-(2,4-dihydroxyphenyl)-1,3,5-triazine (50 g) is suspended in 250 ml 2-ethoxyethanol and heated to 90° C. Benzyltriphenylphosphonium chloride (0.56 g) is added, followed by portionwise addition of ethylenecarbonate (30.6 g) over 6 hours. The mixture is stirred at 135° C. for 10 hours then cooled to room temperature. The crystals formed are filtered off, washed with 100 ml cold methanol and 100 ml water, dried under reduced pressure to give 2-(4-methoxyphenyl)-4,6-[2-hydroxy-4-(2-hydroxyethoxy)-phenyl]-1,3,5-triazine with mp. 180° C.

Example A9

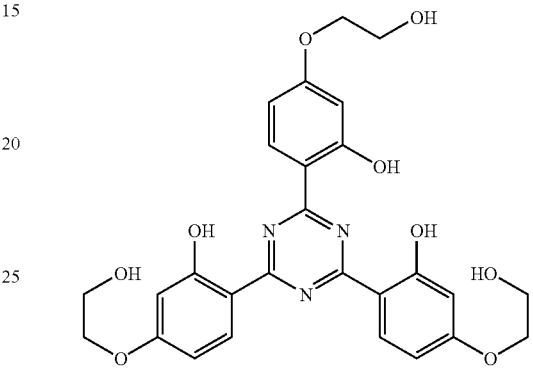

2,4,6-tris-(2-hydroxy-4-(2-hydroxyethoxy)-phenyl]-1,3,5-triazine 2,4,6-tris-(2,4-dihydroxyphenyl)-1,3,5-triazine (50 g) is suspended in 300 ml 2-ethoxyethanol and heated to 70° C. Potassium carbonate (102 g) is added followed by 2-bromo-ethanol (123.4 g) and the mixture heated at 100° for 7 hours. The reaction mixture is cooled to 0° C. and the crystals filtered off, washed with 100 ml cold methanol, 100 ml water and dried under reduced pressure to give 2,4,6-tris-[2-hydroxy-4-(2-hydroxyethoxy)-phenyl]-1,3,5-triazine (40.5 g) with mp 195 ° C.

USE EXAMPLES

Example B1

The UV absorber of formula I is incorporated into the polyol component (Macrynal® SM 510 n) of a 2K polyurethane clearcoat in an amount of 2% relative to the total coating solids. Addition of the isocyanate (Desmodur® N 75) is effected immediately before application of the coating.

Formulation

| a) Polyol | |
|---|---|
| Macrynal ® SM 510n (60%)[1)] | 75.0 g |
| Butyl glycolacetate | 15.0 g |
| Solvesso ® 100[2)] | 6.1 g |
| Methyl isobutyl ketone | 3.6 g |

| | |
|---|---|
| Zn-Octoate (8% metal) | 0.1 g |
| BYK ® 300[3)] | 0.2 g |
| Total Weight (a) | 100.0 g |
| b) Isocyanate | |
| Desmodur ® N 75[4)] | 40.0 g |

[1)]Polyol crosslinker from Vianova Resins GmbH, Germany (new: Solutia GmbH)
[2)]aromatic hydrocarbon mixture, boiling range 182–203° C. (Solvesso 150) or 161–178° C. (Solvesso 100); manufacturer: ESSO
[3)]Antiblocking agent (Byk Chemie GmbH, Germany)
[4)]Isocyanate resin; Bayer AG.

The coating is applied in conventional manner to glass plates and stoved at 80° C. for 45 min. Resulting dry film thickness is 20 µm. UV absorption spectrum is recorded in the range 280–420 nm. Samples are stored for 10 days at 150° C. in an oven. Content of UV absorber is controlled by new recording of UV absorption spectrum.

In none of the coating samples containing compounds Nos. 2, 3 or 5, or a mixture of ca. 6 parts by weight of compound No. 8 and 4 parts by weight of compound No. 9, any loss of UV absorber is detected after oven storage.

Example B2

An unstabilized 2 K—polyurethane reference clear coat formulation is prepared according to the following composition:

| | |
|---|---|
| Macrynal SM 510n (60% supply form)[1)] | 75.0 g |
| Butylgycol acetate | 15.0 g |
| Solvesso 100[2)] | 6.1 g |
| Methyl isobutyl ketone | 3.6 g |
| Zn octoate catalyst (8% metal) | 0.1 g |
| BYK 300[3)] | 0.2 g |
| Total polyol component | 100.0 g |

Prior to application 40 g Desmodur N 75[4)] (isocyanate component) are added to the above polyol component. The resulting clear coat formulation (solids content: 50%) is subsequently processed as the stabilized formulation described below.

For preparation of stabilized formulations a certain quantity of the hydroxyl functional polyol resin (here: Macrynal SM 510n; average hydroxyl content of the solid resin: 4.5%) is replaced by a certain amount of a multi hydroxyl functional UV—absorber as disclosed in the present invention. The exact quantities thereby depend on the hydroxyl content both of the polyol resin and the accessible hydroxyl groups of the UV—absorber. In the present example one half of the Macrynal SM 510 n resin (supply form) is left out, which translates to 37.5 g supply form (=22.5 g solid resin containing approx. 1 g hydroxyl groups). The amount of replacing UV—absorber is then calculated on equal basis, i.e. through the hydroxyl groups accessible for crosslinking (=10 g UV—absorber containing approx. 1 g accessible hydroxyl groups). The resulting formulation is described below:

| | |
|---|---|
| Macrynal SM 510n (60% supply form)[1)] | 37.5 g |
| UV absorber of Example A3 (cpd. No. 11) | 10.0 g |
| Butylgycol acetate | 15.0 g |
| Solvesso 100[2)] | 6.1 g |
| Methyl isobutyl ketone | 3.6 g |
| Zn octoate catalyst (8% metal) | 0.1 g |
| BYK 300[3)] | 0.2 g |
| Total polyol component | 72.5 g |

Prior to application 40 g Desmodur N 75[4)] (isocyanate component) are added to the above polyol component. The resulting clear coat formulation (solids content: 62.5%) is subsequently processed as described below.

The resulting clear coat formulation is subsequently sprayed at a dry film thickness of 40 µm onto aluminium panels (10×30 cm) precoated with a silver metallic basecoat. After application the clear coat is cured at 80° C. for 45 minutes. All samples visually show a good coating quality and hardness.

The panels are then exposed in a Xe-Weather-O-Meter® (CAM 180 cycle according to SAEJ 1960). The 20° gloss (DIN 67 530) and color change (DIN 6174) are monitored as a function of the exposure time.

Good results are also obtained when compound No. 11 is replaced by an equivalent amount (with respect to aliphatic hydroxyl groups) of compound No. 6, 8, 9 or 10.

Raw Materials Used:
[1)] Macrynal SM 510 n: acrylic polyol resin (ca. 4.5% hydroxyl content based on solid resin); Supplier: Solutia (formerly Vianova Resins)
[2)] Solvesso 100: aromatic hydrocarbon; supplier: Exxon
[3)] BYK 300: levelling agent; supplier: BYK—Chemie
[4)] Desmodur N 75: isocyanate component; supplier: Bayer AG Example B3

An unstabilized Dual Cure 2K—UV curable clear coat formulation reference is prepared according to the following composition (amounts in parts by weight):

| | |
|---|---|
| Desmophen ® A 870 | 11.38 |
| Desmophen ® VP LS 2089 | 21.23 |
| Butylacetate | 32.03 |
| Byk ® 306 | 0.55 |

After mixing the four components 2.7 % Irgacure® 184+ 0.3% Irgacure® 819 are added and dissolved in the formulation.

Prior to application 31.09 g of Roskydal® UA VP LS 2337 (isocyanate component) are added to the above polyol component. The resulting clear coat formulation (solids content: 58%) is subsequently sprayed at a dry film thickness of 40 µm onto aluminium panels (10×30 cm) precoated with a silver metallic basecoat. After application the clear coat is cured at 120° C. for 10 minutes followed by a UV-exposure with two mercury medium pressure lamps 120 W at 5 m/min and the panels are then exposed in a Xe-Weather-o-meter® (CAM 180 cycle according to SAEJ 1960). The 20° gloss (DIN 67 530) and color change (DIN 6174) are monitored as a function of the exposure time.

For preparation of stabilized formulations a certain quantity of the hydroxyl functional polyester resin (here: Desmophen® A VP LS 2089; average hydroxyl content of the solid resin: 6%) is replaced by a certain amount of a multi hydroxyl/acrylate functional UV—absorber as disclosed in the present invention. The exact quantities thereby depend on the hydroxyl content both of the polyol resin and the accessible hydroxyl groups of the UV—absorber. In the present example one half of the Desmophen A VP LS 2089 resin (supply form) is left out, which translates to 10.6 g supply form (=7.96 g solid resin containing approx. 0.47 g hydroxyl groups). The amount of replacing UV—absorber is then calculated on equal basis, i.e. through the hydroxyl groups accessible for crosslinking (=9.4 g UV—absorber containing approx. 0.47 g accessible hydroxyl groups). The resulting formulation is described below:

| | |
|---|---|
| Desmophen ® A 870 | 11.38 Parts by weight |
| Desmophen ® VP LS 2089 | 10.6 |
| UV absorber (acrylate/OH functional)* | 9.4 |
| Buthylacetate | 32.03 |
| Byk ® 306 | 0.55 |

*mixture of compounds of Examples A3 and A6 (1:1 by weight)

After mixing the four components 2.7% Irgacure® 184+ 0.3% Irgacure® 819 are added and dissolved in the formulation.

Prior to application 30.5 g Roskydal® UA VP LS 2337 (isocyanate component) are added to the above polyol component. The resulting clear coat formulation is subsequently processed as the unstabilized formulation described above. After cure, all samples visually show a good coating quality and hardness.

Good results are also obtained when the mixture of compounds of Examples A3 and A6 is replaced by an equivalent amount (with respect to the total of aliphatic hydroxyl groups and acrylate groups) of the compound of Example A5.

Raw Materials Used:

| | |
|---|---|
| Desmophen ® A 870 | 70% Hydroxy functional polyacrylate in butylacetate (Bayer AG) |
| Desmophen ® VP LS 2089 | 75% Polyesterpolyol resin in butylacetate (Bayer AG) |
| Roskydal ® UA VP LS 2337 | Isocyanate containing urethane acralate resin (Bayer AG) |
| Byk ® 306 | Flow additive (Byk Chemicals) |
| Irgacure ® 184 | Photoinitiators (Ciba Specialty Chemicals) |
| Irgacure ® 819 | |

Example B4

Polyesters

Analytical Procedures:

Intrinsic Viscosity (I.V.): 1 g polymer is dissolved in 10 g of a mixture of phenol/di-chloro-benzene (1/1). The viscosity of this solution is measured at 30° C. in an Ubelode-viscosimeter and recalculated to the intrinsic viscosity.

Color: Color (b value of the Yellowness Index) is measured according to ASTM D1925 (DIN 5033). Following instrument is used: Minolta Spektrophotometer C M–3600 d Extraction: 1 g PET powder is stirred at ambient temperature for 72 h in 100 g dichloromethane, which is a good solvent for the added UV-absorbers but a poor solvent for PET. The remaining PET is filtered, dried and 0.1 % dissolved in hexafluoroisopropanol.

UV-Spectrum: The PET-substance is milled to a fine powder, which is dissolved in hexafluoroisoproanol with a concentration of 0.1% (wt/volume). The UV-Spectra are measured in Lambda 2 Perkin Elmer between 190 and 600 nm relative to the pure solvent. The UV-absorption coefficient is calculated at the corresponding peak maximum by dividing the absorption by the concentration (unit mg/ml)

PET Synthesis:

Comparative Example (i)

1654 g ethylene glycol, 3322.6 g terephthalic acid, 83.1 g isophthalic acid and 1.36 g antimony trioxide are mixed within a metal container. The mixture is transferred into a 10 l reactor (stainless steel) fitted with stirrer, refluxing unit and an outlet-die at the bottom of the reactor. The reactor can be either pressurized with nitrogen up to 6 bars or—operated under vacuum down to 1 mbar. The monomer mixture is heated from room temperature to 250° C. within 30 min. During heating phase pressure is increased up to 4 bars. A water/ethylene glycol mixture is distilled off for 3.5 h. Temperature is increased consecutively to 280° C. Within next 5 h pressure is continuously reduced to further distill off water and ethylene glycol. Then, polyester product is extruded through the bottom die, cooled to room temperature in a water bath and pelletized to yield clear PET granules.

Typically, by this procedure, a PET is synthesized with following properties:

I.V.: 0.75 dl/g;

Color: b=4

UV-absorption coefficient: there is no absorption above 320 nm

Comparative Example (ii)

The general procedure, as described in the comparative example (i), is repeated with the only difference that 11.93 g (24.54 mmol) of a commercial UV absorber is added (compound of the formula

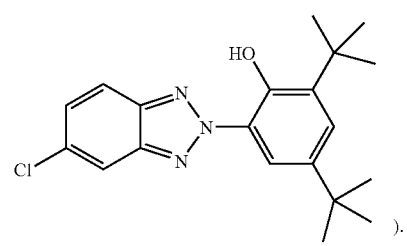

).

Hereby, a PET is synthesized with following characteristics:

UV-absorption coefficient after extraction: there is no significant UV-absorption above 325 nm. This shows that the UV absorber is not bound into the PET chain and is completely removed by the extraction.

Example of the Invention

The general procedure, as described in the comparative example (i), is repeated with the only difference that the compounds listed in following table are added.

| | Amount, Additive No. | I.V. dl/g | Pellet color b-value | UV absorption coefficient before extraction | UV absorption coefficient after extraction |
|---|---|---|---|---|---|
| A | 40.2 g Compound No. 5 | 0.27 | 14 | 0.693 at 332 nm | 0.661 at 332 nm |
| B | 12.06 g (24.54 mmol) Compound No. 5 | 0.68 | 10 | 0.193 at 337 nm | 0.148 at 337 nm |

Nearly constant UV absorption before and after extraction shows that the instant UV-absorbers are incorporated into the PET-chain.

Example B4

Polycarbonate

Analytical Procedures:

Gel permeation chromatography: Polymers are characterized by gel-permeation-chromatography (GPC), with a Hewlett Packard HP 1090 LC, column PSS 1, length 60 cm, elution with tetrahydrofurane (THF), rate 1 ml/min, concentration 10 mg polymer in 1 ml THF, Calibration with styrene. Polydispersity is calculated from Mn (g/mol) and Mw (in g/mol) as PD=Mw/Mn.

UV-Spectrum: The PC-substance is milled to a fine powder, which is dissolved in dichloromethane with a concentration of 0.1% (wt/volume). The UV-Spectra are measured in Lambda 2 Perkin Elmer between 190 and 600 nm relative to the pure solvent. The UV-absorption coefficient of the most red-shifted absorption band is reported and calculated at the corresponding peak maximum by dividing the absorption by the concentration (unit mg/ml).

Polycarbonate (PC) Synthesis:

Comparative Exapmle (i)

17.2 g Bisphenol A, 16.1 g diphenylcarbonate and 0.187 g dibutyltinoxide is mixed in a 100 ml glass flask, fitted with stirrer and distillation unit. The mixture is heated within 1 h to 190° C., additional 5 h at 190° C. Within the next 3 h the pressure is continuously reduced down to 5 mbar and temperature consecutively increased up to 250° C. Progress of polycondensation is monitored by distilling-off phenol. The raw product is purified by completely dissolving in dichloromethane and subsequent precipitation in methanol.

Typically, by this procedure, a PC is synthesized with following properties:
Mn: 5,300 g/mol; Mw: 9,600 g/mol
UV-absorption coefficient: No absorption above 300 nm

Example of the Invention

The general procedure, as described in the comparative example (i), is repeated with the only difference that compounds listed in following table are added.

| Amount; Additive No. | Mn [g/mol] | Mw [g/mol] | UV absorption coefficient |
|---|---|---|---|
| 0.067 g Compound No. 5 | 5,200 | 11,700 | 0.283 at 353 nm |

The absorption at 353 nm observed after purification shows that the current UV-absorber is incorporated into the PC-chain.

Example B5

Reactive Extrusion

Predried PET (M&G Cleartuf AQUA) is physically blended with a UV-absorber at a prescribed weight percentage, thoroughly mixed, then fed to a 27 mm Leistritz co-rotating intermeshing twin screw extruder operated at an average setpoint temperature of 250° C. The extruder is equipped with a monolayer five inch sheet die. The extrusion screw speed, slit dimension of the die, and speed of chiller rolls is adjusted to achieve a 9 mil (229 micron) thick film in each formulation.

The extruder can be operated with vacuum takeoff to facilitate the removal of volatiles and reaction coproducts from the reactive UV additive with the polyester.

Samples of each film are for measurement of the UV light transmission and film color. The UV light transmission spectra are collected on a Perkin Elmer UV/VIS-01 model Lambda 2, scan speed 240 nm/min. Color of the PET films is measured on a DCI SF-600 spectrophotometer, illuminant d65 10 degrees in transmittance mode.

| additive | Weight Percent In PET | % UV light transmission at wavelength | | PET film color | | |
|---|---|---|---|---|---|---|
| | | 375 nm | 390 nm | L* | a* | b* |
| neat PET | 0 | 100 | 100 | 97.1 | −0.2 | 2.2 |
| comp. No. 5 | 0.30 | 14.8 | 35.2 | 97.8 | −0.4 | 2.6 |
| comp. No. 5 | 0.40 | 6 | 21.8 | 97.6 | −0.5 | 2.7 |
| Heatwave ® PET CF746 | 0 | 64.6 | 74.4 | 97.0 | −0.2 | 2.3 |

The PET films containing the compounds of the invention demonstrate superior light blocking capability at and below 390 nm, in comparison to a state of the art comparative Heatwave CF746 polyester containing a UV-blocking technology as described by Eastman (http://wvw.voridian.com/Brands/Heatwave/Heatwave Intro.asp). The PET films provide acceptably low color compared to a standard unstabilized PET and the competitive Heatwave CF746, with the b* yellowness axis values all between 2 and 3 measured units.

Example B6

PET Bottles

PET concentrates (10% by weight) of the UV-absorbers of the table below are prepared using Eastapak 9921W PET, on a 27 mm twin screw extruder at an operating temperature at die of 275° C. The UV absorbers are reacted into the PET under the extrusion conditions.

The concentrates are letdown with base resin to the final additive loading indicated in the table below. PET is dried in vacuo for at least 4 hours at 240° F. prior to preform molding. Preforms are molded on a unit cavity Arburg press using the minimum injection temperature and back pressure necessary to obtain parts free of haze an crystallinity. Bottle blow molding is conducted using a Sidel SBO 2/3 blow molding machine, using preforms described above. Bottle wall thickness of 0.015–0.016 inches is achieved.

| Formulation | UV Absorber | weight % on resin |
|---|---|---|
| 1 (control) | none | |
| 2 (control) | Tinuvin ® 327 | 0.3 |
| 3 (control) | Chimassorb ® 81 | 0.3 |
| 4 | UVA (11) | 0.3 |
| 5 | 1:1 mix of Tinuvin ® 928 and UVA (11) | 0.3 |

The molded bottles represent 16–20 oz. water or soda type PET bottles and 200 mL cough syrup type PET bottles.

Example B7

To formulations 4–5, each of the following additional stabilizers are also added:

5-chloro-2-(2-hydroxy-3-α-cumyl-5-tert-octylphenyl)-2H-benzotriazole;

2-(2-hydroxy-3-α-cumyl-5-tert-octylphenyl)-2H-benzotriazole;

5-trifluoromethyl-2-(2-hydroxy-3-α-cumyl-5-tert-octylphenyl)-2H-benzo-triazole;

5-trifluoromethyl-2-(2-hydroxy-5-tert-octylphenyl)-2H-benzotriazole;

5-trifluoromethyl-2-(2-hydroxy-3,5-di-tert-octylphenyl)-2H-benzotriazole;

5-butylsulfonyl-2-(2-hydroxy-3-α-cumyl-5-tert-octylphenyl)-2H-benzotriazole;

5-trifluoromethyl-2-(2-hydroxy-3-α-cumyl-5-tert-butylphenyl)-2H-benzo-triazole;

5-trifluoromethyl-2-(2-hydroxy-3,5-di-tert-butylphenyl)-2H-benzotriazole;

5-trifluoromethyl-2-(2-hydroxy-3,5-di-α-cumylphenyl)-2H-benzotriazole;

5-butylsulfonyl-2-(2-hydroxy-3,5-di-tert-butylphenyl)-2H-benzotriazole;

5-phenylsulfonyl-2-(2-hydroxy-3,5-di-tert-butylphenyl)-2H-benzotriazole;

5-chloro-2-(2-hydroxy-3,5-di-tert-butylphenyl)-2H-benzotriazole;

2-hydroxy-4-octyloxybenzophenone;

3-α-cumyl-2-hydroxy-5-t-octylphenyl-2H-benzotriazole;

2-(2-hydroxy-3,5-di-α-cumyl)-2H-benzotriazole;

5-chloro-2-(2-hydroxy-3-tert-butyl-5-methylphenyl)-2H-benzotriazole and 4,6-diphenyl-2-(4-hexyloxy-2-hydroxyphenyl)-s-triazine.

Each of the stabilized resin compositions are then blow or injection molded into a PET bottle having incorporated therein each of the UV absorbers. The PET bottles are especially effective at protecting the contents therein from UV radiation, allowing a longer shelf life of the product.

Example B8

To separate poly(ethylene terephthalate), PET, resin formulations are added 0.5% by weight of each of the s-triazine stabilizers (c1)–(c15) described in the specification.

Each of the stabilized resin compositions are then blow or injection molded into a PET bottle having incorporated therein each of the UV absorbers. The PET bottles are especially effective at protecting the contents therein from UV radiation, allowing a longer shelf life of the product.

Example B9

A multi-layer bottle is prepared wherein the exterior layer and the innermost layer contacting the contents are composed of PET and which also comprises a barrier layer. When one or more of the reactable s-triazines (1)–(11) or (c1)–(c15) of the present invention are incorporated via condensation reaction into any of the PET layers at 0.5% by weight based on the weight of the resin, the contents of the bottle are effectively protected from UV radiation.

What is claimed is:

1. A process for crosslinking an organic polymer by reacting a monomer, oligomer and/or polymer with a crosslinking agent, characterized in that the crosslinking agent is of the formula I' or I'';

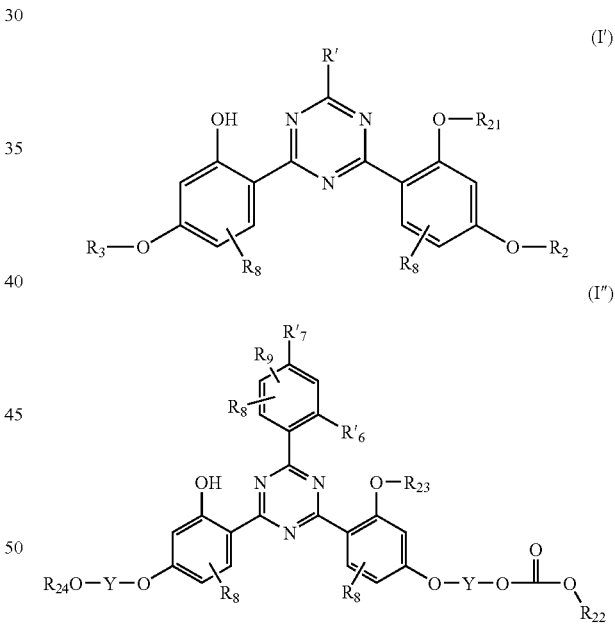

in which

R' is H, $C_1$–$C_{12}$alkyl; $C_5$–$C_{12}$cycloalkyl; $C_2$–$C_{18}$alkyl which is interrupted by one or more O;

$SR_4$; $OR_5$; or is a group of formula II or III;

-continued

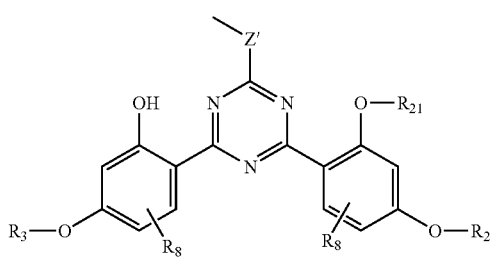
(III)

R₂ and R₃ each are —Y—T;
R₄ is C₁–C₈alkyl; or phenyl;
R₅ is C₁–C₁₂alkyl; C₅–C₁₂cycloalkyl; or C₂–C₁₈alkyl which is interrupted by one or more —O—;
R₆ is H; OH; C₁–C₁₂alkyl; C₅–C₁₂cycloalkyl; or O—Y—T;
R'₆ is H; OH; C₁–C₁₂alkyl; C₅–C₁₂cycloalkyl; or —O—Y—O—CO—O—R₂₂;
R₇ is H; OH; C₁–C₁₂alkyl; C₅–C₁₂cycloalkyl; phenyl; OR₁₀; OCO—R₁₁; NR₁₂—CO—R₁₁; or SR₄;
R'₇ is H; OH; C₁–C₁₂alkyl; C₅–C₁₂cycloalkyl; phenyl; OR'₁₀;
R₈ and R₉ independently are H or C₁–C₁₂alkyl or C₇–C₁₂aralkyl;
R₁₀ is C₁–C₁₂alkyl; C₂–C₁₀alkenyl; C₅–C₁₂cycloalkyl; Y—T; or a group of the formula V;

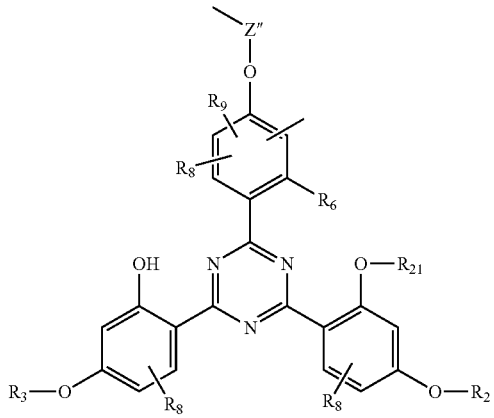
(V)

R'₁₀ is C₁–C₁₂alkyl; C₂–C₁₀alkenyl; C₅–C₁₂cycloalkyl; or —Y—O—CO—O—R₂₂;
R₁₁ is C₁–C₁₂alkyl; C₅–C₁₂cycloalkyl; C₂–C₆alkenyl; or C₁–C₁₂alkoxy;
R₁₂ is H; C₁–C₁₂alkyl; or C₅–C₁₂cycloalkyl;
R₁₃ is C₁–C₁₈alkyl; phenyl; C₇–C₁₂alkylphenyl; or benzyl;
R₂₁ is —Y—T; and when R' is the group

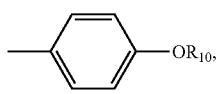

R₂₁ is H or —Y—T;
R₂₂ is phenyl or naphthyl, or phenyl or naphthyl each of which is substituted by C₁–C₁₈alkyl, C₅–C₁₂cycloalkyl, or phenyl;
R₂₃ is H or Y—O—CO—O—R₂₂;
R₂₄ is H or CO—O—R₂₂;

T is OH or —OCO—CH=CH₂ or —OCO—C(CH₃)=CH₂;
Y is C₁–C₁₂alkylene; C₃–C₁₂alkylene substituted by OH or OR₁₃; or C₄–C₁₂alkylene interrupted by O; and T is linked to a primary carbon atom;
Z' is C₁–C₁₂alkylene; C₂–C₁₂alkylene interrupted by O; —O—(C₂–C₁₂alkylene)—O—; or —S—(C₂–C₁₂alkylene)—S—; and
Z" is C₁–C₁₂alkylene; C₂–C₁₂alkylene interrupted by O.

2. A process according to claim 1 wherein in the compound of the formula I' R' is H, C₁–C₁₂alkyl; C₅–C₁₂cycloalkyl; C₂–C₁₈alkyl which is interrupted by one or more O; SR₄; OR₅; or is a group of formula II or III;

(II)

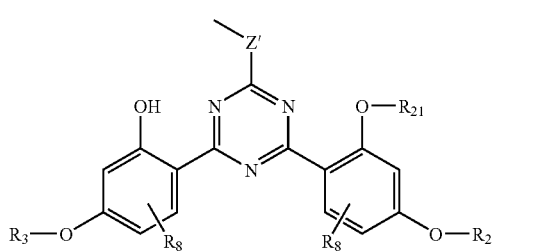
(III)

R₂, R₂₁ and R₃ independently of one another, are H or —Y—OH;
R₄ is C₁–C₈alkyl; or phenyl;
R₅ is C₁–C₁₂alkyl; C₅–C₁₂cycloalkyl; or C₂–C₁₈alkyl which is interrupted by one or more —O—;
R₆ is H; OH; C₁–C₁₂alkyl; C₅–C₁₂cycloalkyl; or O—Y—OH;
R₇ is H; OH; C₁–C₁₂alkyl; C₅–C₁₂cycloalkyl; phenyl; OR₁₀; OCO—R₁₁; NR₁₂—CO—R₁₁; or SR₄;
R₈ and R₉ independently are H or C₁–C₁₂alkyl;
R₁₀ is C₁–C₁₂alkyl; C₂–C₁₀alkenyl; Y—OH; or a group of the formula V;

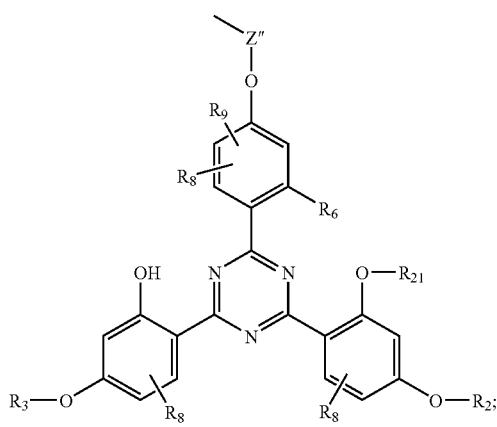
(V)

R₁₁ is C₁–C₁₂alkyl; C₅–C₁₂cycloalkyl; C₂–C₆alkenyl; or C₁–C₁₂alkoxy;

$R_{12}$ is H; $C_1$–$C_{12}$alkyl; or $C_5$–$C_{12}$cycloalkyl;

$R_{13}$ is $C_1$–$C_{18}$alkyl; phenyl; $C_7$–$C_{12}$alkylphenyl; or benzyl;

Y is $C_1$–$C_{12}$alkylene; $C_3$–$C_{12}$alkylene substituted by OH or $OR_{13}$; or $C_4$–$C_{12}$alkylene interrupted by O;

Z' is $C_1$–$C_{12}$alkylene; $C_2$–$C_{12}$alkylene interrupted by O; —O—($C_2$–$C_{12}$alkylene)—O—; or —S—($C_2$–$C_{12}$alkylene)—S—; and Z" is $C_1$–$C_{12}$alkylene; or $C_2$–$C_{12}$alkylene interrupted by O.

3. A process according to claim 1, where in the compound of formula I'R' is a group of formula II;

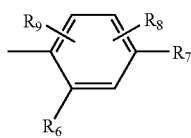
(II)

$R_2$, $R_{21}$ and $R_3$ independently of one another, are H or —Y—T;

$R_6$ is H; OH; or $C_1$–$C_4$alkyl;

$R_7$ is H; OH; $C_1$–$C_4$alkyl; phenyl; or $OR_{10}$;

$R_8$ is H, $C_1$–$C_{12}$alkyl or $C_7$–$C_{11}$phenylalkyl;

$R_9$ is H;

$R_{10}$ is $C_1$–$C_{12}$alkyl; Y—T; or a group of the formula V; and

Y is $C_1$–$C_{12}$alkylene; $CH_2$—CH(OH)—$CH_2$; $CH_2$—CH($CH_2OR_{13}$)—; or $C_4$–$C_{18}$alkylene interrupted by O.

4. A process according to claim 1, where in the compound of formula I'R' is a group of formula II;

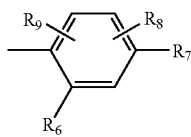
(II)

$R_2$ and $R_3$ independently of one another, are —Y—T;

$R_{21}$ is H or —Y—T;

$R_6$ is H; OH; methyl; or —OY—T;

$R_7$ is H; OH; methyl; phenyl; or $OR_{10}$;

$R_8$ and $R_9$ are H;

$R_{10}$ is $C_1$–$C_{12}$alkyl; Y—T;

T is OH or —OCO—CH=$CH_2$ or —OCO—C($CH_3$)=$CH_2$ or is $OCOOR_{20}$, wherein $R_{20}$ is phenyl or phenyl substituted by $C_1$–$C_8$alkyl; and Y is $C_2$–$C_{12}$alkylene; $CH_2$—CH(OH)—$CH_2$; or $CH_2$—CH($CH_2OR_{13}$)—.

5. A process according to claim 1, where in the compound of formula I' Y is unbranched $C_2$–$C_{12}$alkylene or said alkylene substituted or O-interrupted, where the 2 bonds are located on the terminal C atoms of said alkylene.

6. A process according to claim 1, where the monomer, oligomer and/or polymer are coating binders or photopolymerizable recording materials selected from the group consisting of acrylates, isocyanates, isocyanurates, polyesters, polyamides, polycarbonates, corresponding blends or copolymers and monomeric or oligomeric precursors thereof.

7. A process according to claim 1 wherein the amount of the crosslinking agent of the formula I is from 0.01 to 25 parts by weight on 100 parts of the crosslinkable monomer, oligomer and/or polymer.

8. A process according to claim 1 wherein the crosslinking reaction is carried out at a temperature from 50 to 400° C. applied for 1 to 60 minutes.

9. A process according to claim 6, where the monomer, oligomer and/or polymer and one or more than one compound of the formula I' are added to a processing apparatus and fusing the mixture to above the melting point, in which process the processing apparatus is a single-screw extruder, twin-screw extruder, planetary-gear extruder, ring extruder or Ko-kneader having at least one vent zone to which underpressure is applied, and where the monomer, oligomer and/or polymer are polyesters, copolyesters or polyester blends.

10. Compound of the formula I' or I";

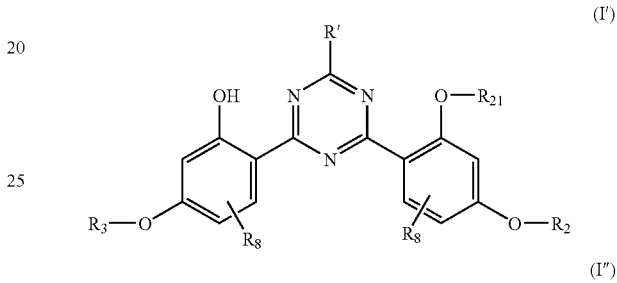
(I')

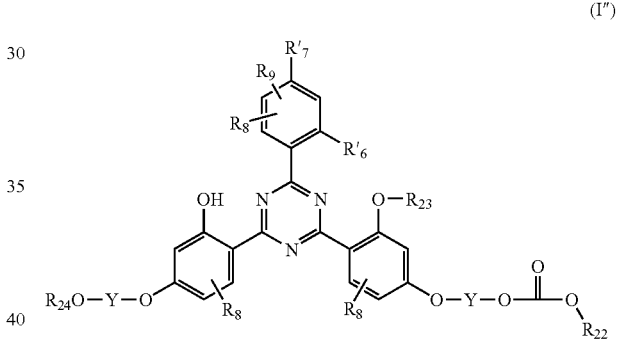
(I")

in which

R' is H, $C_1$–$C_{12}$alkyl; $C_5$–$C_{12}$cycloalkyl; $C_2$–$C_{18}$alkyl which is interrupted by one or more O;

$SR_4$; $OR_5$; or is a group of formula II or III;

(II)

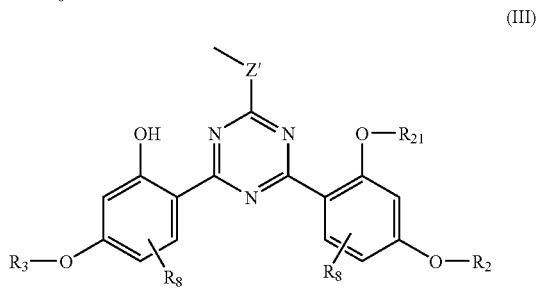
(III)

$R_2$ and $R_3$ each are —Y—T;

$R_4$ is $C_1$–$C_8$alkyl; or phenyl;

$R_5$ is $C_1$–$C_{12}$alkyl; $C_5$–$C_{12}$cycloalkyl; or $C_2$–$C_{18}$alkyl which is interrupted by one or more —O—;

$R_6$ is H; OH; $C_1$–$C_{12}$alkyl; $C_5$–$C_{12}$cycloalkyl; or O—Y—T;

$R'_6$ is H; OH; $C_1$–$C_{12}$alkyl; $C_5$–$C_{12}$cycloalkyl; or —O—Y—O—CO—O—$R_{22}$;

$R_7$ is H; OH; $C_1$–$C_{12}$alkyl; $C_5$–$C_{12}$cycloalkyl; phenyl; $OR_{10}$; OCO—$R_{11}$; $NR_{12}$—CO—$R_{11}$; or $SR_4$;

$R'_7$ is H; OH; $C_1$–$C_{12}$alkyl; $C_5$–$C_{12}$cycloalkyl; phenyl; $OR'_{10}$;

$R_8$ and $R_9$ independently are H or $C_1$–$C_{12}$alkyl or $C_7$–$C_{12}$aralkyl;

$R_{10}$ is $C_1$–$C_{12}$alkyl; $C_2$–$C_{10}$alkenyl; $C_5$–$C_{12}$cycloalkyl; Y—T; or a group of the formula V;

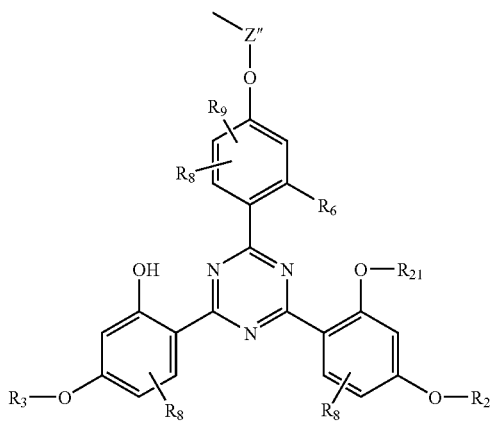

(V)

$R'_{10}$ is $C_1$–$C_{12}$alkyl; $C_2$–$C_{10}$alkenyl; $C_5$–$C_{12}$cycloalkyl; or —Y—O—CO—O—$R_{22}$;

$R_{11}$ is $C_1$–$C_{12}$alkyl; $C_5$–$C_{12}$cycloalkyl; $C_2$–$C_6$alkenyl; or $C_1$–$C_{12}$alkoxy;

$R_{12}$ is H; $C_1$–$C_{12}$alkyl; $C_5$–$C_{12}$cycloalkyl;

$R_{13}$ is $C_1$–$C_{18}$alkyl; phenyl; $C_7$–$C_{12}$alkylphenyl; benzyl;

$R_{21}$ is —Y—T; and when R' is the group

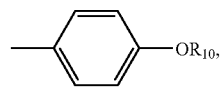

$R_{21}$ is H or —Y—T;

or where $R_{10}$ is a group of formula V, $R_{21}$ is H or —Y—T;

$R_{22}$ is phenyl or naphthyl, or phenyl or naphthyl each of which is substituted by $C_1$–$C_{18}$alkyl, $C_5$–$C_{12}$cycloalkyl, or phenyl;

$R_{23}$ is H or Y—O—CO—O—$R_{22}$;

$R_{24}$ is H or CO—O—$R_{22}$;

T is OH or —OCO—CH=$CH_2$ or —OCO—C($CH_3$)=$CH_2$;

Y is $C_1$–$C_{12}$alkylene; $C_3$–$C_{12}$alkylene substituted by OH or $OR_{13}$; or $C_4$–$C_{12}$alkylene interrupted by O; and T is linked to a primary carbon atom;

Z' is $C_1$–$C_{12}$alkylene; $C_2$–$C_{12}$alkylene interrupted by O; —O—($C_2$–$C_{12}$alkylene)—O—; or —S—($C_2$–$C_{12}$alkylene)—S—; and Z" is $C_1$–$C_{12}$alkylene; $C_2$–$C_{12}$alkylene interrupted by O.

11. A compound according to claim 10 of the formula

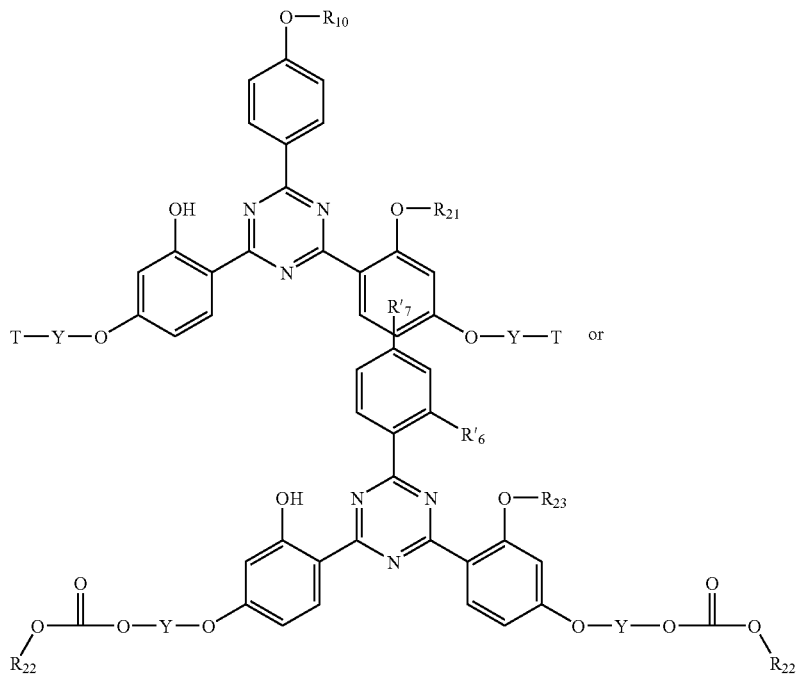

wherein
- $R'_6$ is H; OH; $C_1$–$C_{12}$alkyl; or —O—Y—O—CO—O—$R_{22}$;
- $R'_7$ is H; $C_1$–$C_{12}$alkyl; phenyl; or $OR'_{10}$;
- $R_{10}$ is $C_1$–$C_{12}$alkyl or Y—T;
- $R'_{10}$ is $C_1$–$C_{12}$alkyl or Y—O—CO—O—$R_{22}$;
- $R_{21}$ is H or Y—T;
- $R_{22}$ is phenyl or naphthyl, or phenyl or naphthyl each of which is substituted by $C_1$–$C_8$alkyl;
- $R_{23}$ is H or Y—O—CO—O—$R_{22}$;
- T is OH or —OCO—CH═$CH_2$ or —OCO—C($CH_3$)═$CH_2$; and
- Y is unbranched $C_2$-$C_{12}$alkylene or $C_4$–$C_{12}$alkylene interrupted by O.

12. A crosslinkable composition comprising
(A) a monomer, oligomer and/or polymer capable to build up a chemical bond with a hydroxyfunctional, acrylfunctional and/or aryloxycarbonyloxy functional crosslinking agent and
(B) a compound of the formula I' according to claim 1 as a crosslinker and stabilizer.

13. A composition according to claim 12 comprising in addition to components (A) and (B) a further additive selected from phenolic antioxidants, phosphites, phosphonites, photoinitiators, sterically hindered amines, hydroxylamines, nitrones, benzofuran-2-ones, thiosynergists, polyamide stabilizers, metal stearates, nucleating agents, fillers, reinforcing agents, lubricants, emulsifiers, dyes, pigments, optical brighteners, flame retardants, antistatic agents, blowing agents and further non-reactive UV absorbers of the benzophenone, 2-hydroxyphenyl-benzotriazole or 2-hydroxyphenyltriazine class.

14. Automobile coating or flexographic printing plate or clear or lightly colored plastic container or film for content storage containing a crosslinked layer obtained according to the process of claim 1.

* * * * *

UNITED STATES PATENT AND TRADEMARK OFFICE
CERTIFICATE OF CORRECTION

PATENT NO. : 7,214,742 B2  Page 1 of 1
APPLICATION NO. : 10/497297
DATED : May 8, 2007
INVENTOR(S) : Thomas Bolle et al.

It is certified that error appears in the above-identified patent and that said Letters Patent is hereby corrected as shown below:

The title page under Item (75) should read:

-- (75) Inventors: Thomas Bolle, Effringen-Kirchen (DE); Andreas Valet, Binzen (DE); David George Leppard, Marley (CH), Markus Grob, Riehen (CH); Dirk Simon, Mutterstadt (DE) --.

Signed and Sealed this

Tenth Day of July, 2007

JON W. DUDAS
*Director of the United States Patent and Trademark Office*